US011602517B2

(12) United States Patent
Cho et al.

(10) Patent No.: US 11,602,517 B2
(45) Date of Patent: Mar. 14, 2023

(54) PHARMACEUTICAL COMPOSITION, COMPRISING POLMACOXIB AND PREGABALIN, FOR TREATMENT OF PAIN

(71) Applicant: CRYSTALGENOMICS, INC., Gyeonggi-do (KR)

(72) Inventors: Jae Pyoung Cho, Gyeonggi-do (KR); Joong Myung Cho, Seoul (KR)

(73) Assignee: CrystalGenomics, Inc., Gyeonggi-do (KR)

(*) Notice: Subject to any disclaimer, the term of this patent is extended or adjusted under 35 U.S.C. 154(b) by 0 days.

(21) Appl. No.: 16/982,137

(22) PCT Filed: Mar. 20, 2019

(86) PCT No.: PCT/KR2019/003225
§ 371 (c)(1),
(2) Date: Sep. 18, 2020

(87) PCT Pub. No.: WO2019/190118
PCT Pub. Date: Oct. 3, 2019

(65) Prior Publication Data
US 2021/0113515 A1    Apr. 22, 2021

(30) Foreign Application Priority Data
Mar. 30, 2018 (KR) .................. 10-2018-0037054

(51) Int. Cl.
*A61K 9/24* (2006.01)
*A61K 31/341* (2006.01)
*A61K 9/20* (2006.01)
*A61K 9/48* (2006.01)
*A61K 31/197* (2006.01)

(52) U.S. Cl.
CPC .......... *A61K 31/341* (2013.01); *A61K 9/2009* (2013.01); *A61K 9/209* (2013.01); *A61K 9/2013* (2013.01); *A61K 9/2018* (2013.01); *A61K 9/2027* (2013.01); *A61K 9/2031* (2013.01); *A61K 9/2054* (2013.01); *A61K 9/4858* (2013.01); *A61K 9/4866* (2013.01); *A61K 31/197* (2013.01)

(58) Field of Classification Search
None
See application file for complete search history.

(56) References Cited

U.S. PATENT DOCUMENTS

| 6,593,368 B2 * | 7/2003 | Magnus-Miller .... A61K 31/195 514/561 |
| 2002/0132850 A1 | 9/2002 | Bartholomaeus et al. |
| 2006/0052364 A1 * | 3/2006 | Hopwood ............ A61K 31/415 514/471 |
| 2008/0260817 A1 * | 10/2008 | Patel ..................... A61P 1/02 424/472 |
| 2013/0089608 A1 | 4/2013 | Chen et al. |
| 2014/0302125 A1 | 10/2014 | Kodgule et al. |
| 2016/0008371 A1 | 1/2016 | Trieu |
| 2016/0120885 A1 * | 5/2016 | Trieu ................... A61K 31/549 424/452 |

FOREIGN PATENT DOCUMENTS

| CA | 2771651 A1 | 4/2011 |
| CA | 2992404 A1 | 1/2017 |
| KR | 10-2004-0085216 A | 10/2004 |
| KR | 10-0495389 B1 | 6/2005 |
| KR | 10-0537707 B1 | 12/2005 |
| KR | 10-2010-0112194 A | 10/2010 |
| KR | 20130078147 A | 7/2013 |
| KR | 10-2017-0135163 A | 12/2017 |
| RU | 2570752 C2 | 10/2015 |
| WO | WO 2000/051685 A1 | 9/2000 |
| WO | WO 2016/192680 A1 | 12/2016 |
| WO | WO 2018/015946 A1 | 1/2018 |
| WO | WO-2018015946 A1 * | 1/2018 ........... A61K 31/197 |

OTHER PUBLICATIONS

Lee et al. "A Randomized, Multicenter, Phase III Trial to Evaluate the Efficacy and Safety of Polmacoxib Compared with Celecoxib and Placebo for Patients with Osteoarthritis"; Clinic in Orthopedic Surgery 9:439-457. (Year: 2017).*
Etoday News, "[BioS] Second Challenge of Biotech No. 1 New Drug 'Acelex', 'Complex'", www.etoday.co.kr/newsview.php?idxno=1469744, Mar. 20, 2017. (English Abstract Only).
International Search Report and Written Opinion for Patent Application No. PCT/KR2019/003225 dated Jun. 25, 2019.
Babul et al., "Efficacy and Safety of Extended-Release, Once-Daily Tramadol in Chronic Pain: A Randomized 12-Week Clinical Trial in Osteoarthritis of the Knee", J Pain Symptom Manag. (Jul. 2004) 28:59-71.
Hirankarn et al., GCG100649, A Novel Cyclooxygenase-2 Inhibitor, , Exhibits a Drug Disposition Profile in Healthy Volunteers Compatible With High Affinity to Carbonic Anhydrase-I/II: Preliminary Dose-Exposure Relationships to Define Clinical Development Strategies. Clin Pharmacol Drug Devel. Oct. 2013;2(4): 379-386.
Kim et al., "Structural Insight into the Inhibition of Carbonic Anhydrase by the Cox-2-selective Inhibitor Polmacoxib (CG100649)", Biochem Biophys Res Commun. (Jul. 2016) 478: 1-6.
Schmidt et al., "CG100649, A Tissue-specific Dual Inhibitor of Cox-2 and Carbonic Anhydrase: Phase 2A Clinical Trial in Hip & Knee Osteoarthritis", Osteoarth Cartilage (2009) 17 Suppl. 1, Abstract 324, p. S173.

(Continued)

*Primary Examiner* — Susan T Tran
(74) *Attorney, Agent, or Firm* — Knobbe Martens Olson & Bear LLP

(57) ABSTRACT

The present invention relates to a composite agent comprising polmacoxib and pregabalin. The present invention relates to a pharmaceutical composition and a drug or pain reliever, which each comprise the two active ingredients of polmacoxib and pregabalin and, more particularly, to a drug or pain reliever for treatment of moderately severe, acute, chronic, or neuropathic pain attributed to inflammation and various factors, an effect thereof, and a use thereof.

19 Claims, 17 Drawing Sheets

(56) References Cited

OTHER PUBLICATIONS

Skarke et al., "Comparative Impact on Prostanoid Biosynthesis of Celecoxib and the Novel Nonsteroidal Anti-Inflammatory Drug CG100649", Clin Pharmacol Thera. (Jan. 2012) 91(6): 986-993.
Tallarida R.J., "Quantitative methods for assessing drug synergism", Genes & Cancer (2011) 2: 1003-1008.
Vengerovsky A.I., "Pharmacological incompatibility", Bulletin Siberian Med. (2003) 2(3): 49-56.
Office Action from Brasilian Patent Application No. 11 2020 017773 3, dated Jul. 8, 2022.
Extended Search Report from European Patent Application No. 19777560.4, dated Jan. 20, 2022.
Office Action from Russian Patent Application No. 2020132923, dated Jul. 7, 2022.

\* cited by examiner

PHARMACEUTICAL COMPOSITION, COMPRISING POLMACOXIB AND PREGABALIN, FOR TREATMENT OF PAIN

CROSS REFERENCE TO RELATED APPLICATIONS

This application is a National Stage filing of PCT Application No. PCT/KR2019/003225 filed Mar. 20, 2019, entitled "Pharmaceutical Composition, Comprising Polmacoxib And Pregabalin, For Treatment Of Pain", which claims priority to Korean Patent Application No. 10-2018-0037054 filed Mar. 30, 2018, both of which are incorporated herein by reference.

BACKGROUND OF THE INVENTION

1. Field of the Invention

The present invention relates to a composition comprising polmacoxib and pregabalin, and more particularly, to a pharmaceutical composition for treatment of pain comprising polmacoxib used as a non-steroidal anti-inflammatory agent and pregabalin used to treat broad-spectrum anticonvulsants and neuropathic pain which shows excellent stability and excellent effect at low content.

2. Description of the Related Art

Pain is defined as an unpleasant sensory and emotional experience associated with actual or potential tissue damage, or described in terms of such damage. It may also refer to sense of pain and sensory impairment caused by stimulation of the area in contact with cerebral cortex and marginal systemic regions through a neuropath consisting of nociceptors and nerve fibers. It can be said a warning response that transmits an abnormality inside or outside the body as a defense means to protect the body. Since pain itself is not a disease, elimination of pain does not cure the disease that causes pain.

Pain is largely divided into perceptual pain caused by damage or inflammation of somatic or visceral tissues, and neuropathic pain occurring after nerve injury. Perceptual pain may include skin pain, visceral pain, somatic pain, perceptual neuralgia, nerve root referred pain, somatic referred pain, and the like, and neuropathic pain may include pain due to peripheral or central nervous system dysfunction. If the pain persists for a long time or if the irritation is too severe, it may interfere with daily life and cause anxiety and fear. Because of this, people with chronic pain often have depression, so these characteristics should be considered in treatment.

Pregabalin has a compound name (S)-(+)-3-(aminomethyl)-5-methyl-hexanoic acid) and a structure of the following formula 1.

[Formula 1]

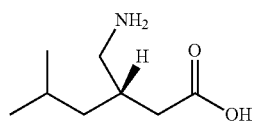

Pregabalin binds to alpha-2-delta (α2δ) subunit of the calcium channel, thereby reducing the influx of calcium ions at the ends of nerve cells and reducing secretion of several excitatory neurotransmitters including glutamate and noradrenalin, thereby restoring the function of nerve cells to normal levels.

Pregabalin is an endogenous neurotransmitter involved in the regulation of brain neuronal activity and is an analogue of γ-amino butyric acid (GABA) involved in nerve processing.

Pregabalin has been found to activate L-glutamate decarboxylase (GAD) and it has a dose-dependent protective effect against seizures and is a central nervous system (CNS) active compound.

Pregabalin can also be useful in anticonvulsant therapy due to the activation of GAD, since it is an amino acid neurotransmitter of gamma-aminobutyric acid which is one of the brain's main inhibitory neurotransmitters released to 30% of brain synapses and causes an inhibitory postsynaptic potential.

These pregabalin drugs can be used to treat epilepsy, neuropathological pain, generalized anxiety disorders, fibromyalgia, and the like.

Causes of neuropathic pain are diabetic multiple neuropathy, post-herpetic neuralgia, tumors, chemotherapy, trigeminal neuralgia, alcohol abuse, vitamin B deficiency, hallucinations, *Borrelia* infection, complex regional pain syndrome, carpal tunnel syndrome, low back pain, and acquired immunodeficiency syndrome.

Pregabalin drug is a white or light yellow crystalline powder that is soluble in water. The drug exhibits rapid and high absorption in the body, reaching maximum blood concentration within 1.3 hours and showing a bioavailability of about 90%. In addition, it is excreted in urine mostly through kidneys and has a half-life of about 5 to 6.5 hours. Pregabalin is absorbed via L-amino acid transport system and has non-uniform absorption in the gastrointestinal tract. Pregabalin is mostly absorbed from the upper part of the small intestine where the L-amino acid transporter is concentrated, so it has the average absorption time of 6 hours. For this reason, many pharmaceutical companies are currently developing tablet formulations such as pregabalin sustained-release tablets, gastroretentive tablets, etc., rather than capsule formulations with low productivity.

Polmacoxib, which is currently commercially available under the name of Acelex capsule, has a structure represented by the following formula 2.

[Formula 2]

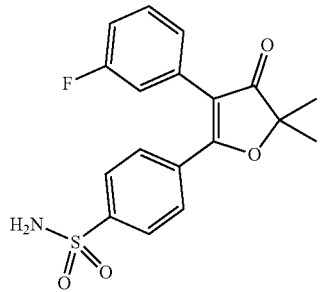

Polmacoxib, an effective ingredient used in the pharmaceutical composition of the present invention, has a compound name of 5-(4-(aminosulfonyl)-phenyl)-2,2-dimethyl-4-(3-fluorophenyl)-3(2H)-furanone. It is a selective inhibitor of COX-2 and has reduced gastrointestinal toxicities than conventional NSAIDs. It is known to be effective in inflammatory disease, inflammation-related disease, pain, solid cancer, angiogenesis-related disease, Alzheimer's disease, seizure and convulsion, stroke, or epilepsy (Korean Patent No. 10-0495389).

COX (cyclooxygenase) is responsible for the production of prostaglandin. Two isoforms, COX-1 and COX-2, have been identified. COX-2 has been shown to be induced by pro-inflammatory stimuli and is an isoform of an enzyme that is assumed to play a major role in the synthesis of prostanoid regulators associated with pain, inflammation, and fever.

The present invention intends to apply a combination of polmacoxib which is a COX-2 inhibitor and pregabalin having these effects to the treatment of acute and chronic pain.

The present invention is focused on a pharmaceutical composition in which the combination of polmacoxib and pregabalin can achieve additional effects in severe to moderate pain, in particular pain associated with inflammation and demonstrating the combination.

SUMMARY OF THE INVENTION

The inventors have aimed to formulate two different active ingredients into a single dosage form in order to further enhance synergistic effects on the pain and dosing convenience over existing products of a combination of polmacoxib and pregabalin.

The present invention provides a pharmaceutical composition comprising polmacoxib and pregabalin for the treatment of pain.

According to one embodiment, the composition may be used for the treatment of acute or chronic pain caused by inflammatory or neuropathy. Specifically, the indication of the composition may comprise neurogenic pain including diabetic neuropathy, pain caused by generalized anxiety disorder, fibromyalgia, hyperalgesia, allodynia, cancer pain, osteoarthritis, rheumatoid arthritis, spondylitis, frozen shoulder, lumbodynia or sciatica.

According to one embodiment, the ratio of polmacoxib to pregabalin may be a weight ratio of 1:1 to 1:600.

In addition, the ratio of polmacoxib to pregabalin may be a weight ratio of 1:1 to 300:1, or a weight ratio of 2:1 to 2:300.

According to one embodiment, the composition may comprise 0.1 to 10% by weight of polmacoxib and 10 to 50% by weight of pregabalin based on the total weight of the composition.

According to one embodiment, the composition may further comprise a pharmaceutically acceptable excipient. Specifically, the excipient may comprise one or more selected from the group consisting of ethyl cellulose, hydroxy propyl cellulose, hydroxy propyl methyl cellulose, sodium carboxy methyl cellulose, polyethylene oxide, carbomer, sodium alginate, mannitol, sodium croscarmellose, sodium hydrogen carbonate and magnesium stearate.

According to one embodiment, the composition may be provided in the form of tablet, capsule or suspension. Specifically, the tablet, capsule or suspension may be a tablet, capsule or suspension with polmacoxib and pregabalin mixed, and the tablet may include a double-layered tablet, a multi-layered tablet, or a single tablet.

In addition, the composition may be formed into the form of a double-layered tablet having a bi-layered structure or a multi-layered tablet having a multi-layered structure in which the polmacoxib, pregabalin or a mixture thereof is separated into an individual layer.

According to one embodiment, the composition may be formed into the form of a double layer divided into a sustained-release layer and an immediate release layer. Specifically, the sustained-release layer may contain pregabalin, and the immediate release layer may contain polmacoxib.

According to one embodiment, the composition may further comprise a pharmaceutically acceptable coating base.

In addition, the composition may further comprise a pharmaceutically acceptable carrier.

Other specific embodiments of the present invention are included in the following detailed description.

Effect of the Invention

According to the pharmaceutical composition for treatment of pain comprising polmacoxib and pregabalin of the present invention, the composition has a similar drug release pattern to each of Lyrica capsules which are commercially available oral formulations comprising pregabalin, and acelex tablets. Specifically, by formulating polmacoxib and pregabalin into a single dosage form, the effect of each drug can be exerted sustainably and complementarily even with taking once or twice a day while minimizing the interaction of each drug interaction in the dosage form.

The composition according to the present invention has stability against external physical factors and improved uniformity due to excellent flowability of particles, and thus it can have easy handling and improved productivity.

DETAILED DESCRIPTION OF THE INVENTION

Figure 1:
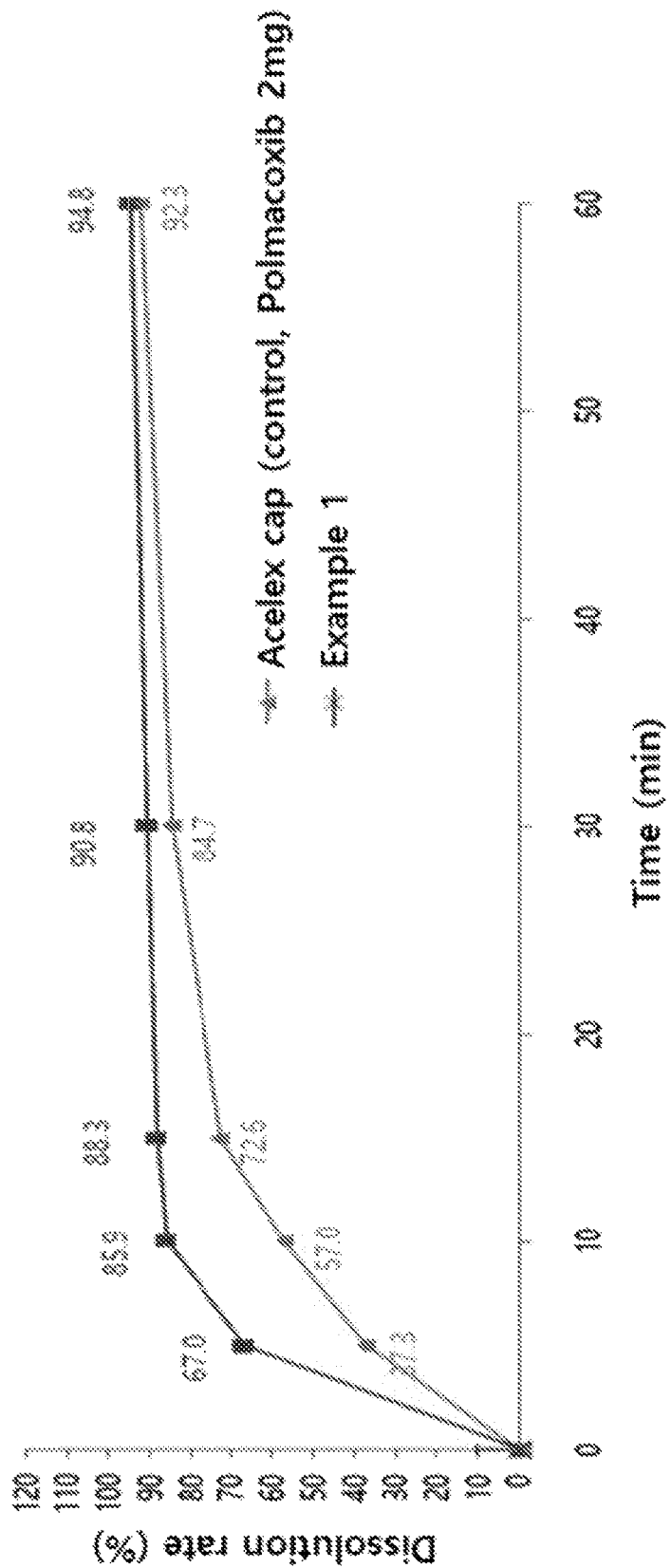
FIG. 1 is a graph showing the comparative dissolution pattern of polmacoxib of Experimental Example 1.

Since various modifications and variations can be made in the present invention, particular embodiments are illustrated in the drawings and will be described in detail in the detailed description. It should be understood, however, that the invention is not intended to be limited to the particular embodiments, but includes all modifications, equivalents, and alternatives falling within the spirit and scope of the invention. In the following description of the present invention, detailed description of known functions will be omitted if it is determined that it may obscure the gist of the present invention.

Hereinafter, the pharmaceutical composition according to the embodiment of the present invention will be described in more detail.

The term "pharmaceutical composition", as used herein may be described interchangeably with "pharmacological composition" and "pharmaceutically acceptable composition" and refers to any composition which can be a relatively non-toxic to a subject to be administered and have harmless effective action. In addition, it may refer to any organic or inorganic compound formulation in that side effects resulting from the composition do not impair the efficacy of the drug, and that does not cause serious irritation to a subject to be administered by the compound and does not impair the biological activities and properties of the compound.

As used herein, the term 'subject to be administered' may be used interchangeably with 'individual to be administered' and 'organism to be administered', and may refer to any animals including humans in which acute or chronic pain is caused or may be caused.

The present invention provides a pharmaceutical composition for treatment of pain comprising polmacoxib and pregabalin. The combination of polmacoxib and pregabalin may exhibit effects of reducing deformation of active ingredients to increase stabilities against changes over time when mixed with other pharmaceutically acceptable additives.

According to one embodiment, the composition may be formulated in liquid or solid form and may be provided in any convenient form, such as in the form of tablets, pellets, granules, capsules, suspensions, emulsions or powders, which is suitable for reconstitution with water or other suitable liquid medium.

For example, the composition may be formed in the form of tablets, pills, capsules, suspensions, and the like. The tablet may include a single-layer tablet, a double-layer tablet, or a multi-layer tablet, and the pills may include a double-layer pill, a multi-layer pill, or a single pill. In addition, for example, it may be formed into a capsule formulation filled with particles, granules, pellets.

Specifically, for example, pregabalin may be produced in the form of a capsule formulation with little influence from external physical factors during the manufacturing process in view of raw material characteristics. In addition, it can be manufactured in a tablet form that minimizes the generation of related substances by manufacturing with a tableting pressure that can improve instability. In addition, a long-term stay in the stomach can effectively act on absorption of the drug in terms of the nature of the mechanism of absorption of the pregabalin component in the body, so it can be prepared as a gastroretentive tablet formulation.

In addition, according to one embodiment, the composition may be formed in the form of a double-layered tablet having a bi-layered structure or a multi-layered tablet having a multi-layered structure in which polmacoxib, pregabalin or a mixture thereof is separated into an individual layer. For example, it may be formed of a double layer or a multi-layer consisting of a sustained-release layer and an immediate release layer, the sustained-layer may contain pregabalin and the immediate release layer may contain polomacoxib.

According to a specific embodiment, the immediate release layer is formed with granules of the mixture of polmacoxib and pregabalin and the sustained-release layer is formed with pregabalin granules and then they can be formulated by a tableting machine. Further, for example, a polmacoxib-containing layer may be formed in the immediate release layer, and a pregabalin layer may be formed in the sustained release layer and then they can be formulated by a tableting machine.

The manufacturing method of the bi-layered structure may comprise, but is not limited to, forming a lower layer with granules of pregabalin and a mixture thereof and compressing, and then forming an upper layer with granules of polmacoxib and a mixture thereof and tableting them using a tableting machine.

According to one embodiment, it may be prepared in a cored tablet formulation containing an inner core of pregabalin layer and an outer core of polmacoxib layer or a cored tablet formulation containing an inner core of polmacoxib layer and an outer core of pregabalin layer. Alternatively, it may be formed into a dual release micro-coating (DRM) containing an outer coating layer of pregabalin layer on an inner layer of polmacoxib layer.

According to one embodiment, the ratio of polmacoxib to pregabalin may be a weight ratio of, for example, 1 to 300:1 to 600, for example 1:1 to 1:300, for example 2:1 to 2:300.

In addition, the composition may comprise 0.1 to 10% by weight of polmacoxib and 10 to 50% by weight of pregabalin, for example 0.3 to 1.0% by weight of polmacoxib and 10 to 30% by weight of pregabalin based on the total weight of the composition. In addition, polmacoxib may be present in an amount of 1 to 5 mg, for example 1 to 2 mg, and pregabalin may be present in an amount of 75 to 300 mg, for example 75 to 150 mg in the composition.

According to one embodiment, the composition may further comprise a pharmaceutically acceptable excipient. For example, the excipient may comprise one or more selected from the group consisting of ethyl cellulose, hydroxy propyl cellulose, hydroxy propyl methyl cellulose, sodium carboxy methyl cellulose, polyethylene oxide, carbomer, sodium alginate, mannitol, sodium croscarmellose, sodium hydrogen carbonate and magnesium stearate. Among them, for example, it may comprise one or more selected from the group consisting of hydroxypropyl methyl cellulose, D-mannitol, hydroxypropyl cellulose, sodium croscarmellose, sodium hydrogen carbonate, and magnesium stearate.

Specifically, in order to improve the mixing uniformity and tableting properties of the polmacoxib active ingredient in the composition in a mixture state, Mannitol 200SD, which a water-insoluble polymer having uniform particles, may be used, but is not limited thereto.

In addition, specifically, when the composition is, for example, a double-layered formulation comprising a sustained-release layer and an immediate release layer, it may comprise one or more selected from the group consisting of hydroxypropyl methyl cellulose, polyethylene oxide (PEO), carbomer, sodium alginate, ethyl cellulose, hydroxy propyl methyl cellulose and sodium carboxy methyl cellulose as a sustained release matrix excipient, for example hydroxypropyl methyl cellulose. In addition, it is possible to increase floating property by inducing the generation of gas on the tablet surface in order to allow the drug to float in the stomach for a certain period of time and stay in the stomach for a long time. At this time, an excipient containing sodium hydrogen carbonate may be used.

According to one embodiment, in consideration of factors affecting gastrointestinal exercise and other sustained-release drug release, the sustained-release agent added with the excipient may be present in an amount of 10 to 70%, for example, 30 to 50% of the total weight of the sustained-release layer. In addition, when sodium hydrogen carbonate, which increases the floating property of the tablet, is added in an amount greater than the appropriate amount, it may rather increase the disintegration of the tablet and interfere with the release of the drug. For example, it may be present in an amount of 1 to 15% based on the total weight of the composition, for example 8 to 12%.

According to one embodiment, the composition may further comprise a coating base to ensure long-term stability of polmacoxib which is light-sensitive and pregabalin which is affected on stability by external factors such as moisture and temperature. As the coating base, for example, a water-soluble coating base may be used, and also a commonly used coating base may be used. Specifically, for example, it includes a coating base including polyvinyl alcohol derivatives, methacrylic acid derivatives and polyacrylic acid derivatives, for example one or two or more selected from the group consisting of Opadry®. Kollicoat®, and hydroxypropyl methylcellulose (HPMC), for example polyvinyl alcohol-containing Opadry® having a relatively excellent moisture and light blocking effect.

According to one embodiment, the composition may further comprise a pharmaceutically acceptable carrier. As a carrier, it is possible to use those commonly used in formulation, for example it includes, but is not limited to, lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methyl cellulose, methyl hydroxyl benzoate, propyl hydroxyl benzoate, talc, magnesium stearate and mineral oil.

According to one embodiment, in addition to the above components, commonly used pharmaceutically acceptable substances, such as fillers, extenders, binders, disintegrants, solubilizers, antiseptics, buffers, glidants, absorbents, coating agents, colorants, water-soluble additives, lubricants, wetting agents, sweeteners, flavoring agents, emulsifiers, suspending agents and preservatives may be included as additional additives. Such additives may be included within a range of contents that minimizes the influence on the effective ingredient of the composition according to the present invention, for example in an amount of 5 to 90 wt %, for example 40 to 90 wt % based on the total weight of the composition.

According to one embodiment, the composition may act on pain, for example acute or chronic pain caused by inflammatory or neuropathy. Specifically, the composition may exhibit an effective action as an analgesic agent for treating neurogenic pain including diabetic neuropathy, pain caused by generalized anxiety disorder, fibromyalgia, hyperalgesia, allodynia, cancer pain, osteoarthritis, rheumatoid arthritis, ankylosing spondylitis, frozen shoulder, lumbodynia or sciatica. For example, the present invention can be used for the treatment of severe to moderate pain associated with inflammatory components such as rheumatoid arthritis, ankylosing spondylitis, sciatica and frozen shoulder.

The pharmacological or pharmaceutical composition according to the present invention may be prepared in any form suitable for application to humans, including infants, children and adult animals, by standard procedures known to those skilled in the art.

Hereinafter, embodiments of the present invention will be described in detail so that those skilled in the art can easily carry out the present invention. The present invention may, however, be embodied in many different forms and should not be construed as limited to the embodiments set forth herein.

Example 1

Excipients without interaction between drug and excipients were selected through compatibility studies with pregabalin main component lacking stability to minimize their types. Polmacoxib and pregabalin as main ingredients and excipients as shown in Table 1 were combined in wet granulation, dried, formulated and mixed, and then filled in the capsule. The mesh net has 30 mesh.

TABLE 1

| Polmacoxib-pregabalin complex (Example 1) | | | | |
|---|---|---|---|---|
| Manufacturing process | Purpose | Material | per tablet (mg) | Content (%) |
| 1 Granulation | Main ingredient | Polmacoxib | 1 | 0.5 |
| 2 | Main ingredient | Pregabalin | 75 | 34.1 |
| 3 | Excipient | D-mannitol(200SD) | 114 | 51.8 |
| 4 | Binder | Hydroxypropyl cellulose(L) | 6 | 2.7 |
| 5 | Solvent | Ethanol | 60 | — |
| 6 Post-mixing | Disintegrant | Sodium croscarmellose | 20 | 9.1 |
| 7 | Lubricant | Magnesium stearate | 4 | 1.8 |
| | Total amount of mixture | | 220 | 100 |
| 8 Filling | Filling | Weight of capsule base | 75 | |
| | Total amount of capsule | | 295 | |

Experimental Example 1

According to Test 2 (Paddle method, device 2) of dissolution test of Korean Pharmacopoeia, in vitro comparative dissolution test was conducted on the formulation of Example 1. As a control, a commercially available product was used. Specifically, a comparative dissolution test was conducted for polmacoxib using Acelex capsule of CrystalGenomics as a control, and a comparative dissolution test was conducted for pregabalin using Lylica capsule as a control.

As the dissolution test medium for the polmacoxib component, 1st fluid with pH 1.2 of the disintegration test method of the Korean Pharmacopoeia 11th edition, which has the largest dissolution difference between Example 1 and the control, was used, the test temperature was 37±0.5° C. and the rotational speed was 50 rpm, and the results are shown in Table 2 and FIG. 1.

Figure 2:
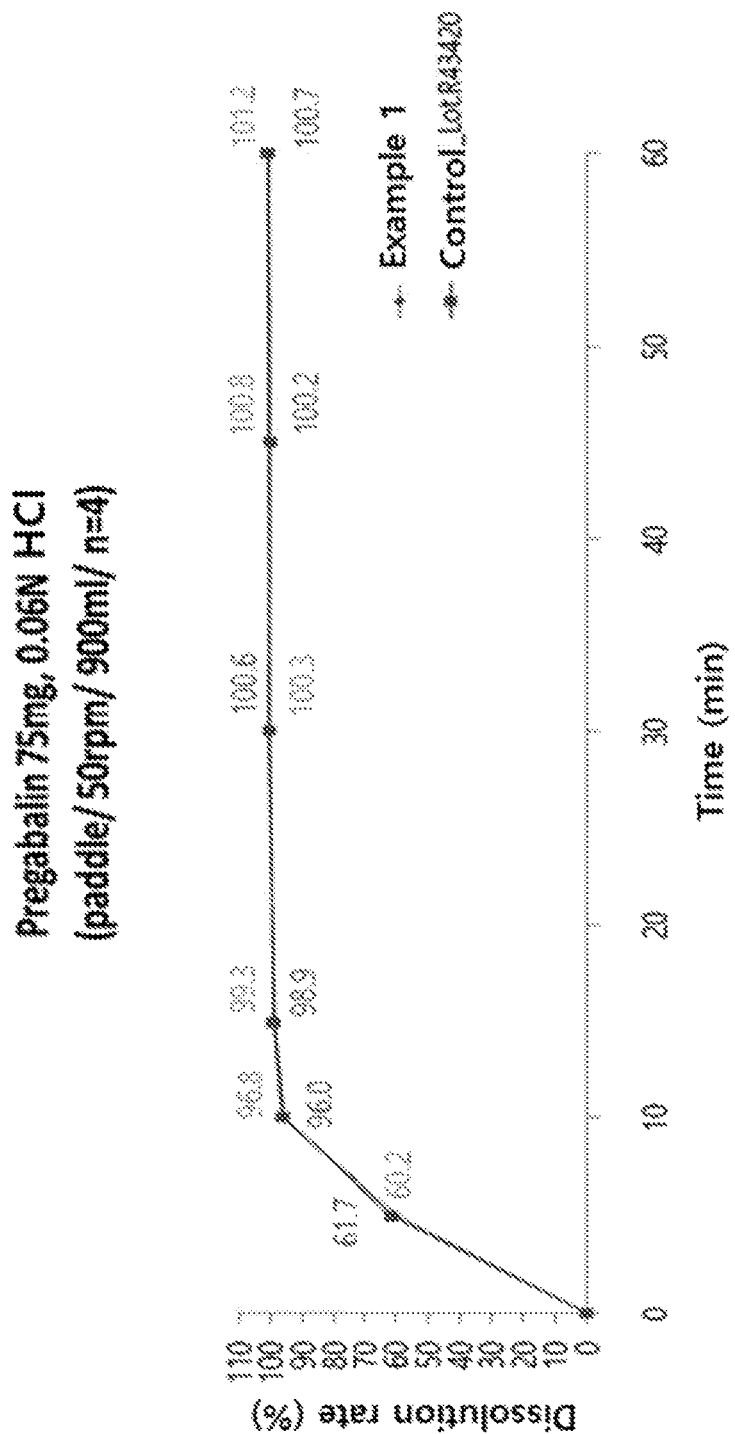
FIG. 2 is a graph showing the comparative dissolution pattern of pregabalin of Experimental Example 1.

In addition, as the dissolution test medium for the pregabalin component, 0.06 N HCl, a dissolution medium for standard and test method was used, since it shows similar patterns in all of 4 dissolution mediums, 1st fluid with pH 1.2 of the disintegration test method of the Korean Pharmacopoeia 11th edition, 0.05 mol/L acetic acid/sodium acetate buffer solution with pH 4.0 of Japanese Pharmacopoeia 17th edition, 2nd fluid with pH 6.8 of the disintegration test method of the Korean Pharmacopoeia 11th edition and water. The results are shown in Table 3 and FIG. 2.

The dissolution rate was expressed as an average value, and the unit was %9.

TABLE 2

| | | Time(min) | | | | | | |
|---|---|---|---|---|---|---|---|---|
| | | 0 | 5 | 10 | 15 | 30 | 45 | 60 |
| Example 1 | Average | 0 | 67.0 | 85.7 | 87.9 | 90.2 | 92.5 | 94.0 |
| Control(Acelex cap) | Average | 0 | 37.2 | 56.8 | 72.4 | 84.3 | 88.5 | 91.7 |

TABLE 3

| | | Time(min) | | | | | | |
|---|---|---|---|---|---|---|---|---|
| | | 0 | 5 | 10 | 15 | 30 | 45 | 60 |
| Example 1 | Average | 0 | 60.2 | 96.8 | 99.3 | 100.3 | 100.8 | 101.2 |
| Control(Lyrica cap) | Average | 0 | 61.7 | 96.0 | 98.9 | 100.6 | 100.2 | 100.7 |

As shown in the table and drawings, a difference in the initial dissolution rate between the composition of Example 1 and the control was observed.

Example 2

The composition was filled in the capsule in the same manner as in Example 1, except that the disintegrant was changed as shown in Table 4.

TABLE 4

| Polmacoxib-pregabalin complex (Example 2) | | | | |
|---|---|---|---|---|
| Manufacturing process | Purpose | Material | per tablet (mg) | Content (%) |
| 1 Granulation | Main ingredient | Polmacoxib | 1 | 0.5 |
| 2 | Main ingredient | Pregabalin | 75 | 34.1 |
| 3 | Excipient | D-mannitol(200SD) | 114 | 51.8 |
| 4 | Binder | Hydroxypropyl cellulose(L) | 6 | 2.7 |
| 5 | Solvent | Ethanol | 60 | — |
| 6 Post-mixing | Disintegrant | Sodium croscarmellose | 10 | 9.1 |
| 7 | Lubricant | Magnesium stearate | 4 | 1.8 |
| | | Total amount of mixture | 220 | 100 |
| 8 Filling | Filling | Weight of capsule base | 75 | |
| | | Total amount of capsule | 295 | |

Experimental Example 2

Comparative dissolution test was conducted on the formulation of Example 2 in the same manner as in Experimental Example 1.

Figure 3:
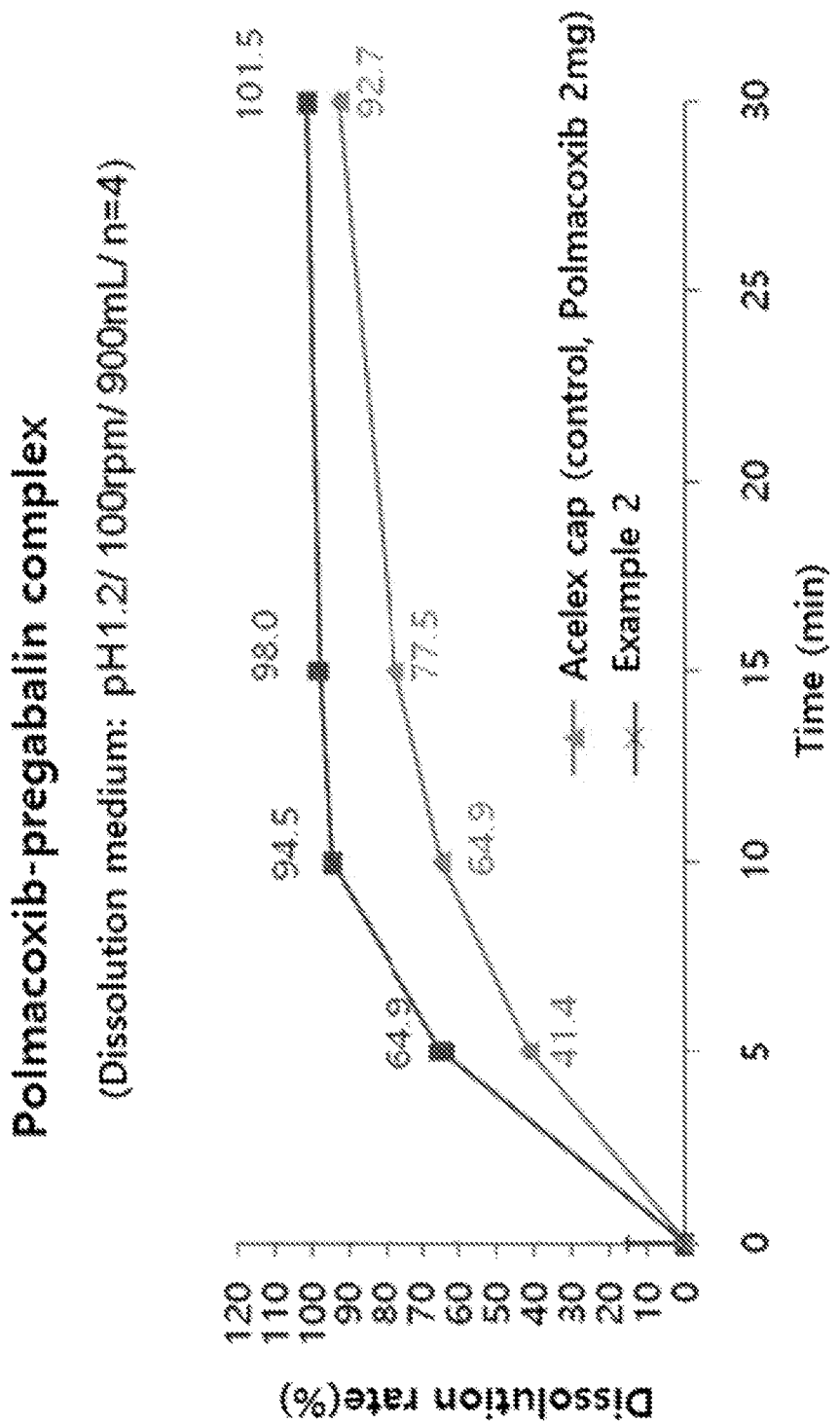
FIG. 3 is a graph showing the comparative dissolution pattern of polmacoxib of Experimental Example 2.
Figure 4:
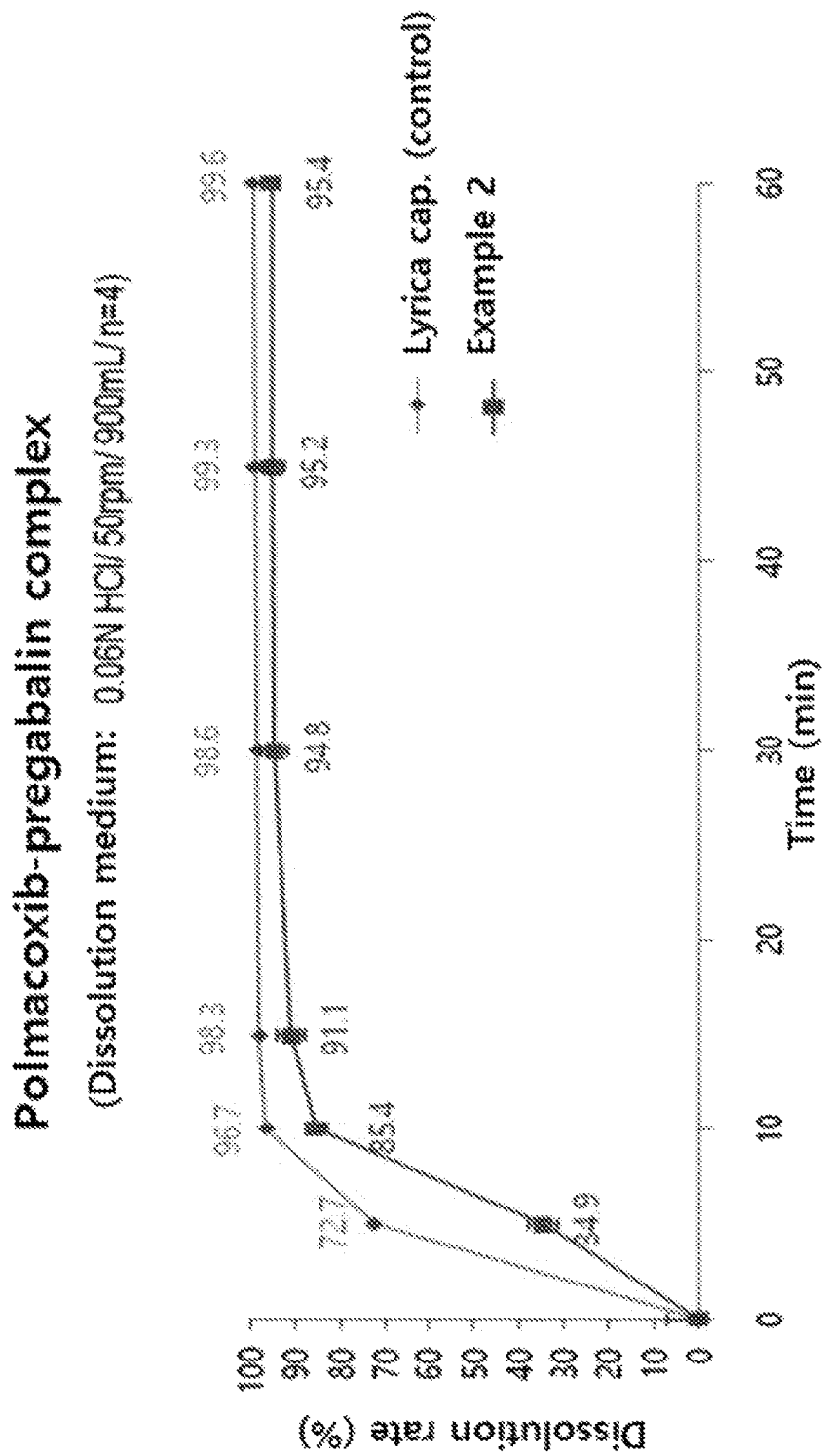
FIG. 4 is a graph showing the comparative dissolution pattern of pregabalin of Experimental Example 2.

The test solution for polmacoxib was pH 1.2 and the results are shown in Table 5 and FIG. 3. The test solution for pregabalin was 0.06 N HCl and the results are shown in Table 6 and FIG. 4.

TABLE 5

| | | Time(min) | | | | |
|---|---|---|---|---|---|---|
| | | 0 | 5 | 10 | 15 | 30 |
| Example 2 | Average | 0 | 64.9 | 94.5 | 98.0 | 101.5 |
| Control (Acelex cap) | Average | 0 | 41.4 | 64.9 | 77.5 | 92.7 |

TABLE 6

| | | Time(min) | | | | | | |
|---|---|---|---|---|---|---|---|---|
| | | 0 | 5 | 10 | 15 | 30 | 45 | 60 |
| Example 2 | Average | 0 | 34.9 | 85.4 | 91.1 | 94.8 | 95.2 | 95.4 |
| Control (Lyrica cap) | Average | 0 | 72.7 | 96.7 | 98.3 | 98.6 | 99.3 | 99.6 |

As shown in the table and drawings, the dissolution difference between pregabalin and the control was increased by disintegrant.

Example 3

The composition of Table 7 was filled in the capsule in the same manner as in Example 1, except that it was treated with a mesh net of 16 or 20 mesh.

TABLE 7

| Polmacoxib-pregabalin complex (Example 3) | | | | |
|---|---|---|---|---|
| Manufacturing process | Purpose | Material | per tablet (mg) | Content (%) |
| 1 Granulation | Main ingredient | Polmacoxib | 1 | 0.5 |
| 2 | Main ingredient | Pregabalin | 75 | 34.1 |
| 3 | Excipient | D-mannitol(200SD) | 114 | 51.8 |
| 4 | Binder | Hydroxypropyl cellulose(L) | 6 | 2.7 |
| 5 | Solvent | Ethanol | 60 | — |
| 6 Post-mixing | Disintegrant | Sodium croscarmellose | 20 | 9.1 |
| 7 | Lubricant | Magnesium stearate | 4 | 1.8 |
| | | Total amount of mixture | 220 | 100 |
| 8 Filling | Filling | Weight of capsule base | 75 | |
| | | Total amount of capsule | 295 | |

Experimental Example 3

Figure 5:
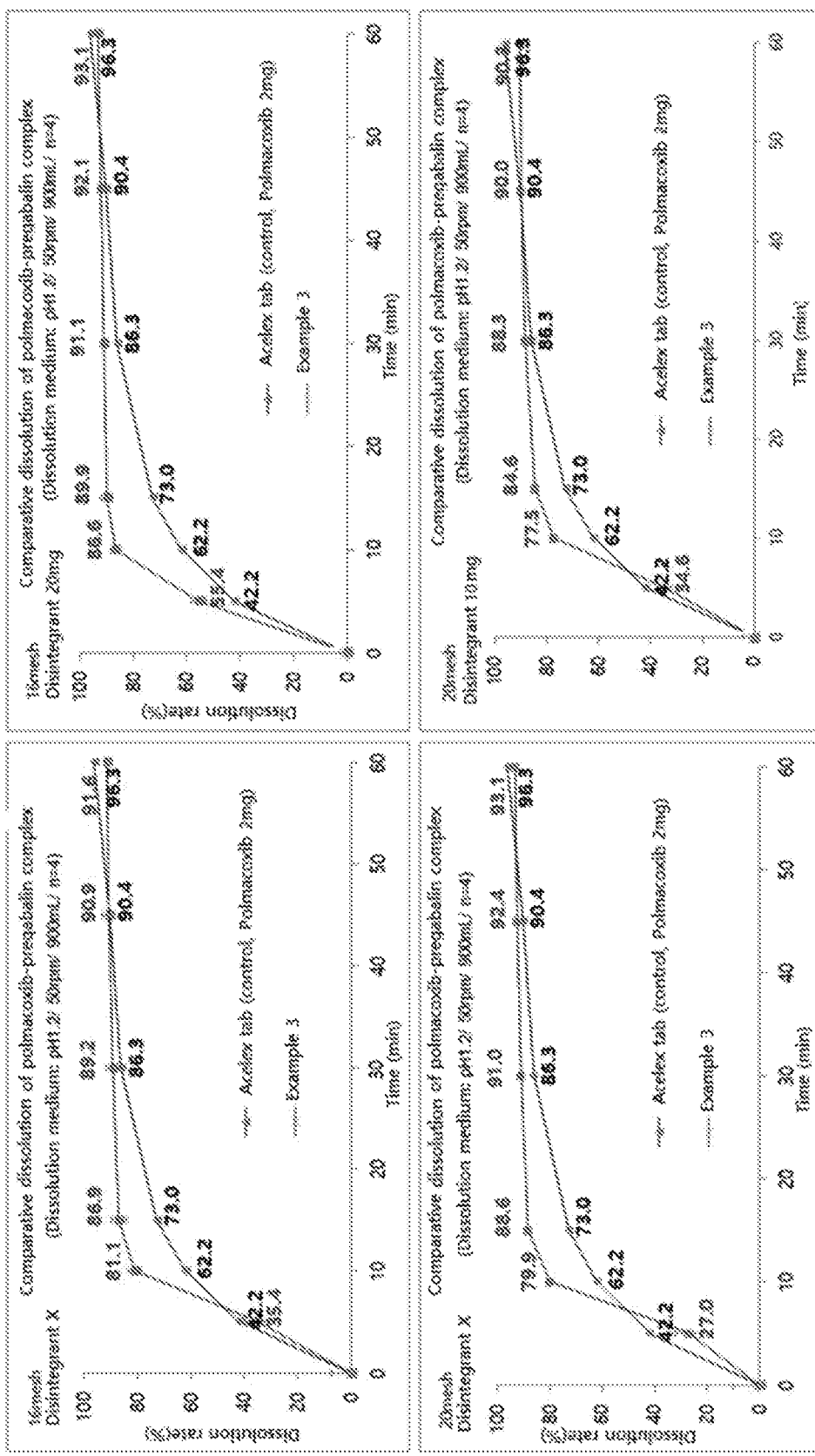
FIG. 5 is a graph showing the comparative dissolution pattern of polmacoxib of Experimental Example 3.

In order to confirm the change in the dissolution rate according to mesh size and the presence of disintegrant during the manufacturing process, a comparative dissolution test was conducted on the polmacoxib of Example 3 in the same manner as in Experimental Example 1. The test solution was pH 1.2 and the control was Acelex capsule, and the results are shown in Table 8 and FIG. 5.

TABLE 8

| | | | | | | Time (min) | | | |
|---|---|---|---|---|---|---|---|---|---|
| | pH 1.2 | | 0 | 5 | 10 | 15 | 30 | 45 | 60 |
| Example 3 | 16 mesh | Average | 0 | 35.4 | 81.1 | 86.9 | 89.2 | 90.9 | 91.6 |
| Control | Disintegrant X | Average | 0 | 42.2 | 62.2 | 73.0 | 86.3 | 90.4 | 96.3 |
| Example 3 | 16 mesh | Average | 0 | 55.4 | 86.6 | 89.9 | 91.1 | 92.1 | 93.1 |
| Control | Disintegrant 20 mg | Average | 0 | 42.2 | 62.2 | 73.0 | 86.3 | 90.4 | 96.3 |
| Example 3 | 20 mesh | Average | 0 | 27.0 | 79.9 | 88.6 | 91.0 | 92.4 | 93.1 |
| Control | Disintegrant X | Average | 0 | 42.2 | 62.2 | 73.0 | 86.3 | 90.4 | 96.3 |
| Example 3 | 20 mesh | Average | 0 | 34.6 | 77.5 | 84.6 | 88.3 | 90.0 | 90.3 |
| Control | Disintegrant 10 mg | Average | 0 | 42.2 | 62.2 | 73.0 | 86.3 | 90.4 | 96.3 |

Example 4

The composition of Table 9 was prepared in the same manner as in Example 3, except that it was prepared in a tablet form. In preparing tablets, the optimal tableting pressure was selected in consideration of instability of pregabalin.

TABLE 9

| Polmacoxib-pregabalin complex (Example 4) | | | | |
|---|---|---|---|---|
| Manufacturing process | Purpose | Material | per tablet (mg) | Content (%) |
| 1 Granulation | Main ingredient | Polmacoxib | 1 | 0.5 |
| 2 | Main ingredient | Pregabalin | 75 | 34.1 |
| 3 | Excipient | D-mannitol(200SD) | 114 | 51.8 |
| 4 | Binder | Hydroxypropyl cellulose(L) | 6 | 2.7 |
| 5 | Solvent | Ethanol | 60 | — |
| 6 Post-mixing | Disintegrant | Sodium croscarmellose | 20 | 9.1 |
| 7 | Lubricant | Magnesium stearate | 4 | 1.8 |
| | | Total amount of mixture | 220 | 100 |

Experimental Example 4

Tablets with different hardness were formulated using the composition of Example 4 and then a comparative dissolution test was conducted for the polmacoxib component in the same manner as in Experimental Example 1.

Figure 6:
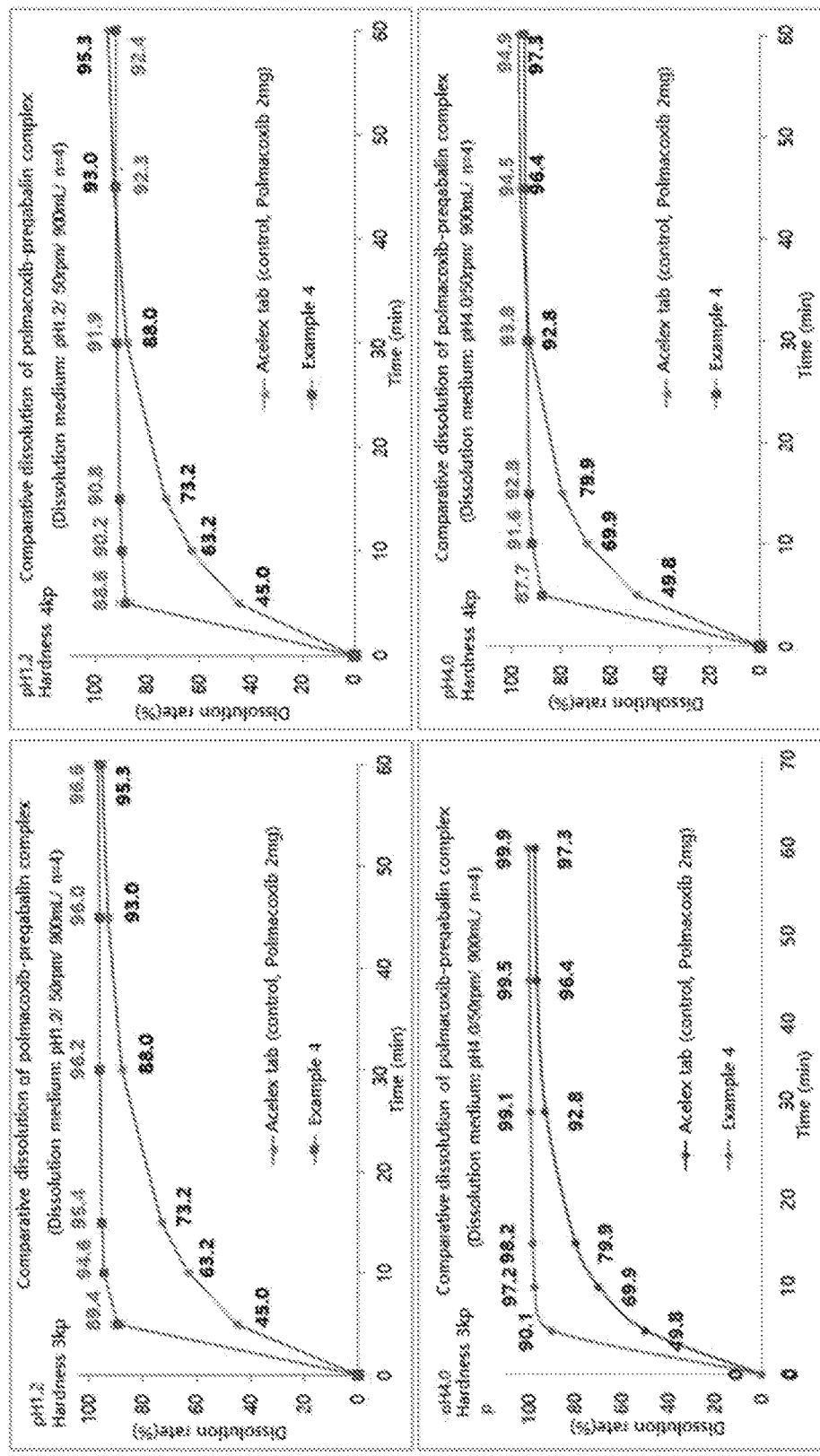
FIG. 6 is a graph showing the comparative dissolution pattern of polmacoxib of Experimental Example 4.

As the dissolution test medium, 1st fluid with pH 1.2 of the disintegration test method of the Korean Pharmacopoeia 11th edition or 0.05 mol/L acetic acid/sodium acetate buffer solution with pH 4.0 of Japanese Pharmacopoeia 17th edition was used and the control was Acelex capsule. The results are shown in Table 10 and FIG. 6.

TABLE 10

|  |  |  | \multicolumn{7}{c}{Time (min)} |
| --- | --- | --- | --- | --- | --- | --- | --- | --- | --- |
|  |  |  | 0 | 5 | 10 | 15 | 30 | 45 | 60 |
| Example 4 | Hardness 3 kp | Avg. | 0 | 89.4 | 94.6 | 95.4 | 96.2 | 96 | 96.6 |
| Control | pH 1.2 | Avg. | 0 | 45 | 63.2 | 73.2 | 88 | 93 | 95.3 |
| Example 4 | Hardness 4 kp | Avg. | 0 | 88.6 | 90.2 | 90.8 | 91.9 | 92.3 | 92.4 |
| Control | pH 1.2 | Avg. | 0 | 45 | 63.2 | 73.2 | 88 | 93 | 95.3 |
| Example 4 | Hardness 3 kp | Avg. | 0 | 90.1 | 97.2 | 98.2 | 99.1 | 99.5 | 99.9 |
| Control | pH 4.0 | Avg. | 0 | 49.8 | 69.9 | 79.9 | 92.8 | 96.4 | 97.3 |
| Example 4 | Hardness 4 kp | Avg. | 0 | 87.7 | 91.6 | 92.8 | 93.8 | 94.5 | 94.9 |
| Control | pH 4.0 | Avg. | 0 | 49.8 | 69.9 | 79.9 | 92.8 | 96.4 | 97.3 |

Experimental Example 5

Figure 7:
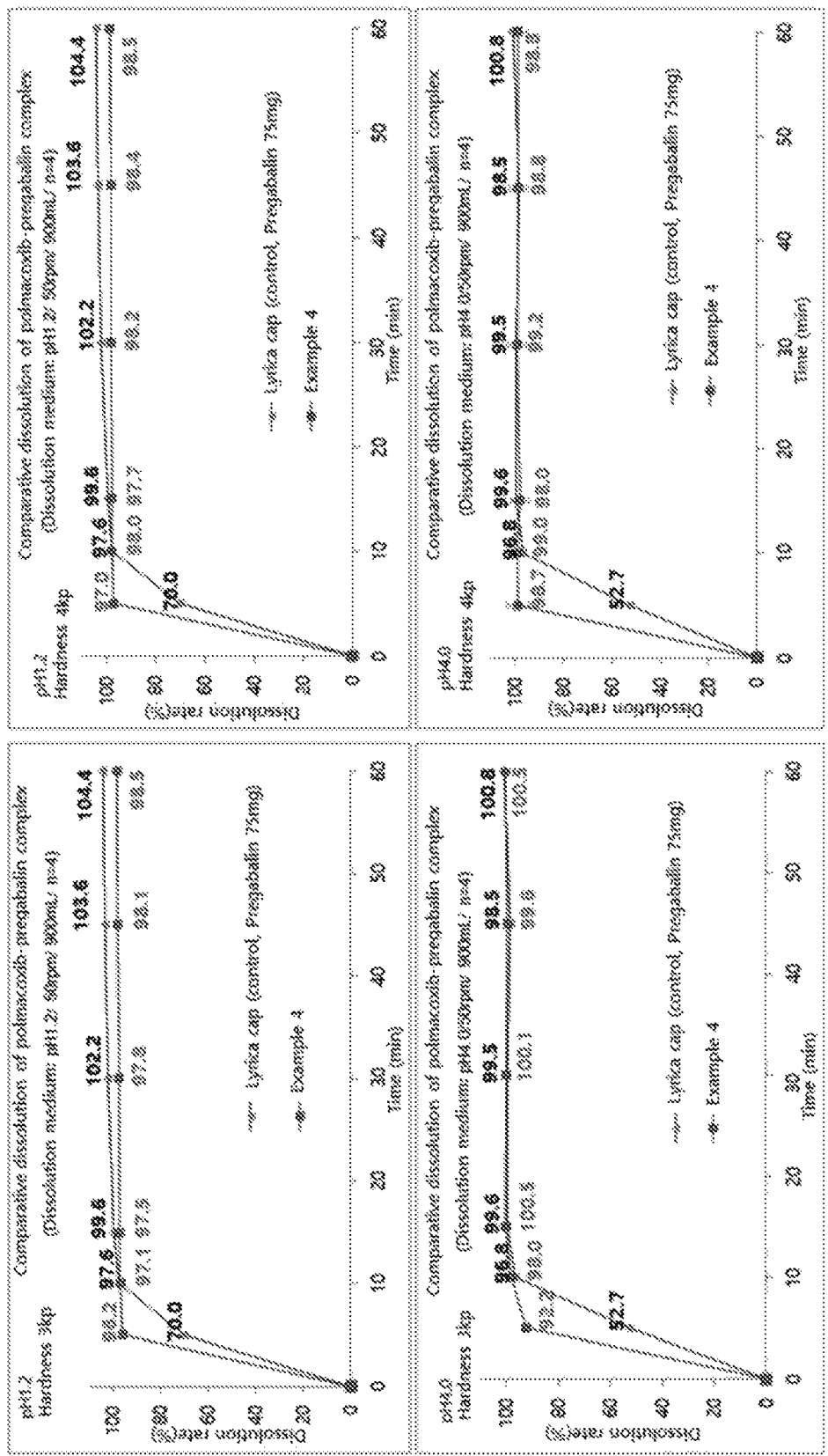
FIGS. 7 and 8 are graphs showing the comparative dissolution pattern of Experimental Example 5.
Figure 8:
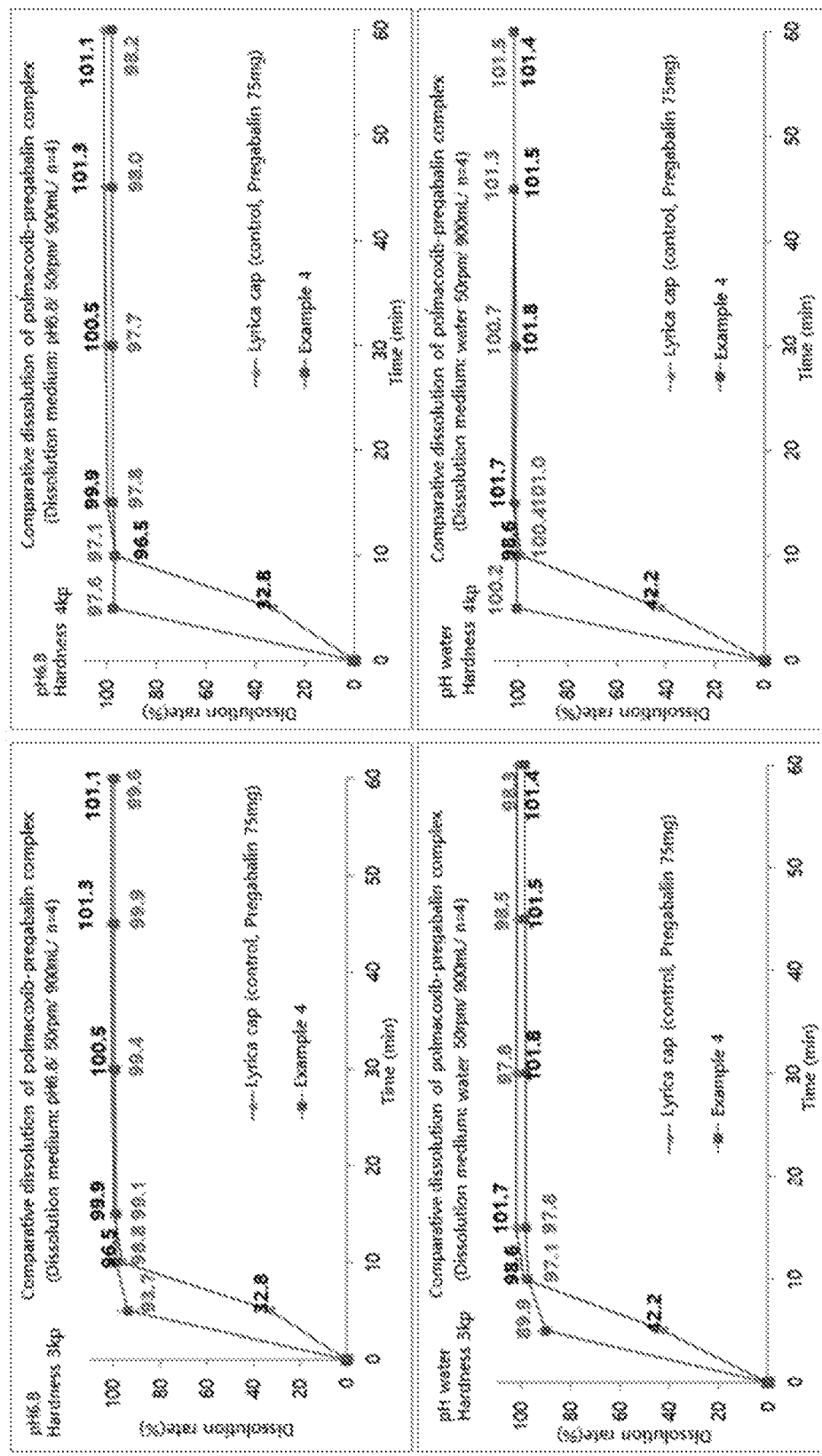

Tablets with different hardness were formulated using the composition of Example 4 and then comparative dissolution test was conducted for the pregabalin component using 1st fluid with pH 0.2 of the disintegration test method of the Korean Pharmacopoeia 11th edition, 0.05 mol/L acetic acid/sodium acetate buffer solution with pH 4.0 of Japanese Pharmacopoeia 17th edition, 2nd fluid with pH 6.8 of the disintegration test method of the Korean Pharmacopoeia 11th edition or water in the same manner as in Experimental Example 1. The control was Lyrica capsule. The results are shown in Table 11, Table 12, FIG. 7 and FIG. 8.

TABLE 11

|  |  |  | \multicolumn{7}{c}{Time (min)} |
| --- | --- | --- | --- | --- | --- | --- | --- | --- | --- |
|  |  |  | 0 | 5 | 10 | 15 | 30 | 45 | 60 |
| Example 4 | Hardness 3 kp | Avg. | 0 | 96.2 | 97.1 | 97.5 | 97.8 | 98.1 | 98.5 |
| Control | pH 1.2 | Avg. | 0 | 70.0 | 97.6 | 99.6 | 102.2 | 103.6 | 104.4 |
| Example 4 | Hardness 4 kp | Avg. | 0 | 97.0 | 98.0 | 97.7 | 98.2 | 98.4 | 98.5 |
| Control | pH 1.2 | Avg. | 0 | 70.0 | 97.6 | 99.6 | 102.2 | 103.6 | 104.4 |
| Example 4 | Hardness 3 kp | Avg. | 0 | 92.2 | 98.0 | 100.5 | 100.1 | 99.6 | 100.5 |
| Control | pH 4.0 | Avg. | 0 | 52.7 | 96.8 | 99.6 | 99.5 | 98.5 | 100.8 |
| Example 4 | Hardness 4 kp | Avg. | 0 | 98.7 | 99.0 | 98.0 | 99.2 | 98.8 | 98.8 |
| Control | pH 4.0 | Avg. | 0 | 52.7 | 96.8 | 99.6 | 99.5 | 98.5 | 100.8 |

TABLE 12

|  |  |  | \multicolumn{7}{c}{Time (min)} |
| --- | --- | --- | --- | --- | --- | --- | --- | --- | --- |
|  |  |  | 0 | 5 | 10 | 15 | 30 | 45 | 60 |
| Example 4 | Hardness 3 kp | Avg. | 0 | 93.7 | 98.8 | 99.1 | 99.4 | 99.9 | 99.6 |
| Control | pH 6.8 | Avg. | 0 | 32.8 | 96.5 | 99.9 | 100.5 | 101.3 | 101.1 |
| Example 4 | Hardness 4 kp | Avg. | 0 | 97.6 | 97.1 | 97.8 | 97.7 | 98.0 | 98.2 |
| Control | pH 6.8 | Avg. | 0 | 32.8 | 96.5 | 99.9 | 100.5 | 101.3 | 101.1 |
| Example 4 | Hardness 3 kp | Avg. | 0 | 89.9 | 97.1 | 97.8 | 97.8 | 98.5 | 98.3 |
| Control | Water | Avg. | 0 | 42.2 | 98.6 | 101.7 | 101.8 | 101.5 | 101.4 |
| Example 4 | Hardness 4 kp | Avg. | 0 | 100.2 | 100.4 | 101.0 | 100.7 | 101.3 | 101.5 |
| Control | Water | Avg. | 0 | 42.2 | 98.6 | 101.7 | 101.8 | 101.5 | 101.4 |

Example 5

Tablets were prepared in the same manner as in Example 4, except that the composition of Table 13 was used in order to improve tableting properties in a production facility when increasing the manufacturing unit of the formulation according to Example 4. Capping may occur in tableting crystalline pregabalin-containing compositions. Therefore, in order to improve it, microcrystalline cellulose having a fine particle size was added, the content of excipients was increased and sodium croscarmellose which had been added in the post-mixing was added in the granulation.

TABLE 13

| Polmacoxib-pregabalin complex (Example 5) | | | | |
|---|---|---|---|---|
| Manufacturing process | Purpose | Material | per tablet (mg) | Content (%) |
| 1 Granulation | Main ingredient | Polmacoxib | 1 | 0.4 |
| 2 | Main ingredient | Pregabalin | 75 | 29.3 |
| 3 | Excipient | D-mannitol(200SD) | 66 | 25.8 |
| 4 | Excipient | Microcrystalline cellulose101 | 90 | 35.2 |
| 5 | Binder | Hydroxypropyl cellulose(L) | 10 | 3.9 |
| 6 | Solvent | Ethanol | 80 | — |
| 7 | Disintegrant | Sodium croscarmellose | 10 | 3.9 |
| 8 Post-mixing | Lubricant | Magnesium stearate | 4 | 1.6 |
| | | Total amount of mixture | 256 | 100 |

Example 6

Tablets were prepared in the same manner as in Example 4, except that the composition of Table 14 was used to further improve tableting properties over the formulation of Example 5. Specifically, the content of excipients was increased, and silicon dioxide was added.

TABLE 14

| Polmacoxib-pregabalin complex (Example 6) | | | | |
|---|---|---|---|---|
| Manufacturing process | Purpose | Material | per tablet (mg) | Content (%) |
| 1 Granulation | Main ingredient | Polmacoxib | 1 | 0.3 |
| 2 | Main ingredient | Pregabalin | 75 | 25.9 |
| 3 | Excipient | D-mannitol(200SD) | 66 | 22.8 |
| 4 | Excipient | Microcrystalline cellulose101 | 120 | 41.4 |
| 5 | Binder | Hydroxypropyl cellulose(L) | 10 | 3.4 |
| 6 | Solvent | Ethanol | 80 | — |
| 7 | Disintegrant | Sodium croscarmellose | 10 | 3.4 |
| 8 | Excipient | Silicon dioxide | 4 | 1.4 |
| 9 Post-mixing | Lubricant | Magnesium stearate | 4 | 1.4 |
| | | Total amount of mixture | 290 | 100 |

Experimental Example 6

A comparative dissolution test was conducted on the formulation of Example 6 in the same manner as in Experimental Example 1. As the dissolution test medium, 1st fluid with pH 1.2 and water were used, the control for polmacoxib was Acelex tablet and the control for pregabalin was Lyrica capsule.

Figure 9:
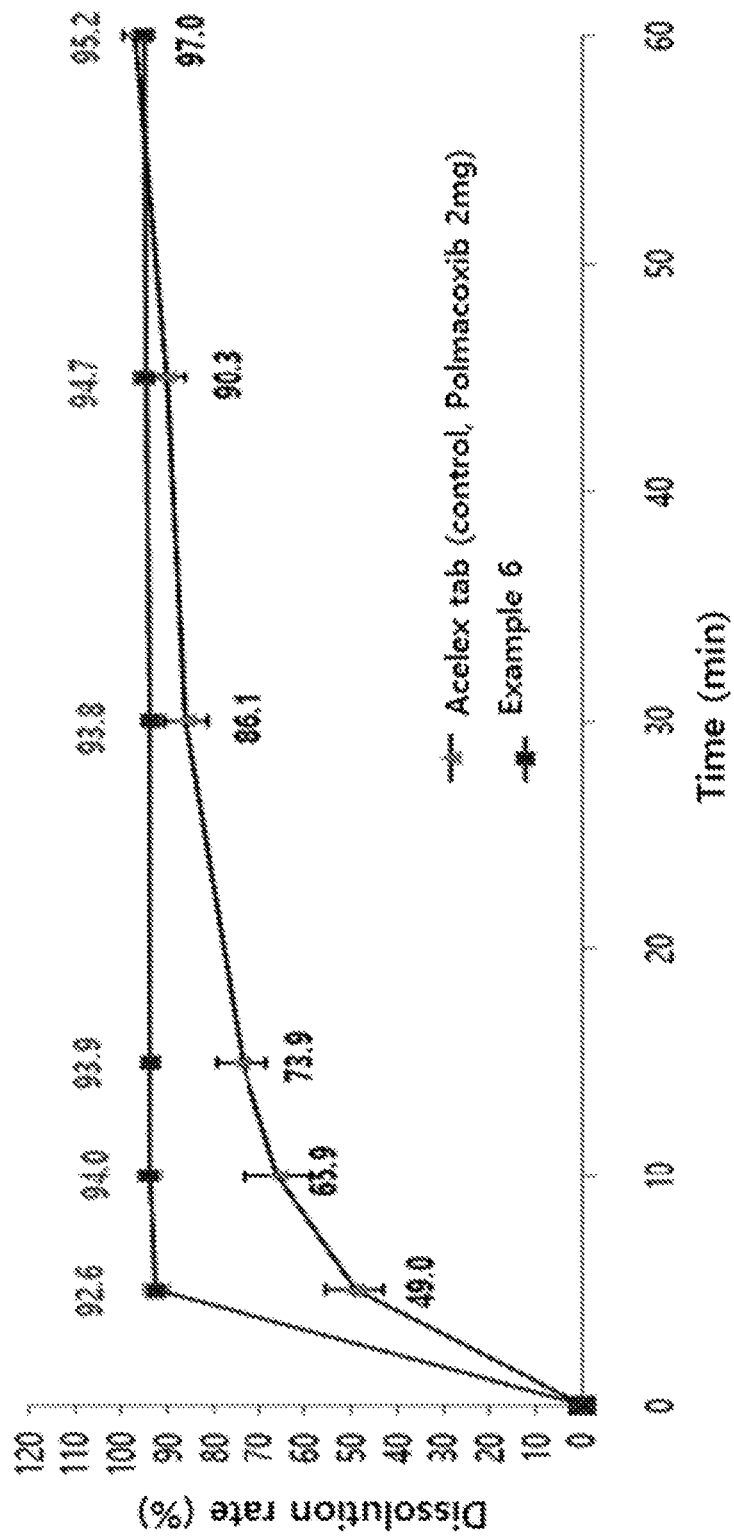
FIGS. 9 and 10 are graphs showing the comparative dissolution pattern of Experimental Example 6.
Figure 10:
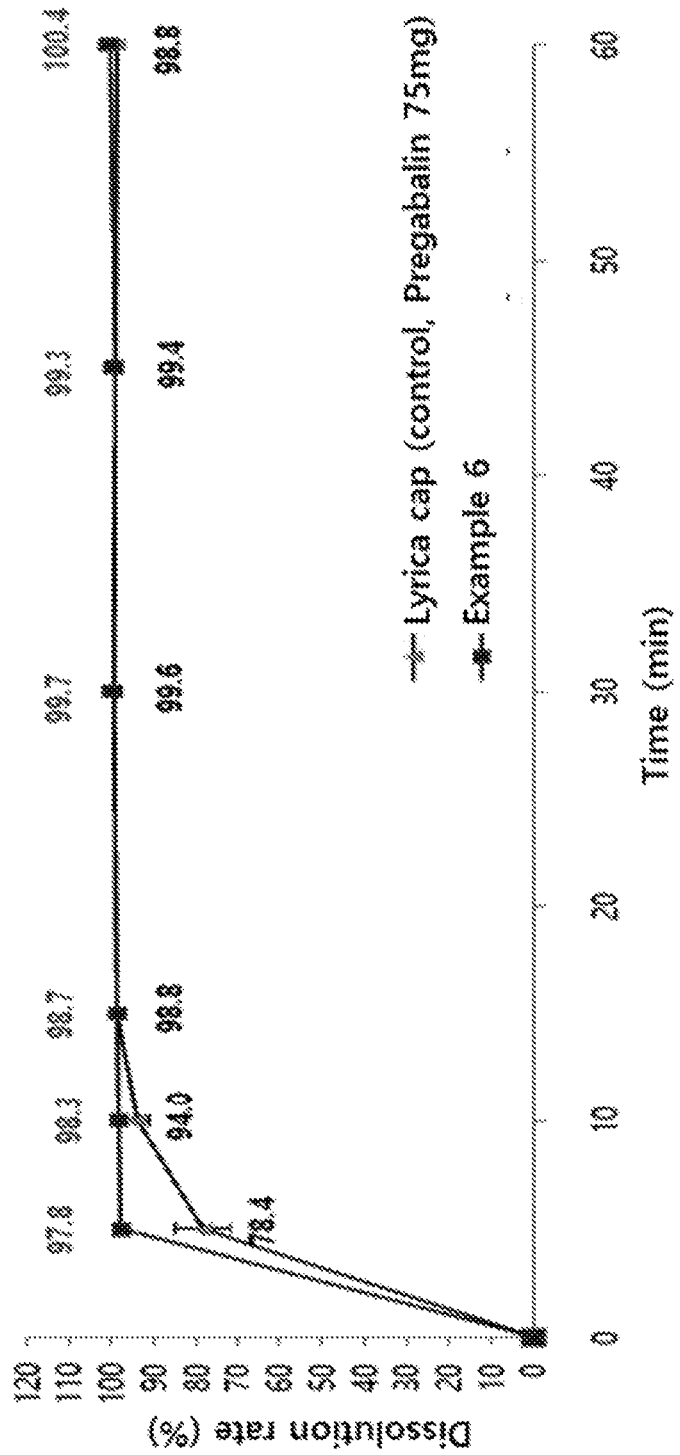

The results of the comparative dissolution test for the polmacoxib component are shown in Table 15 and FIG. 9 and the results of the comparative dissolution test for the pregabalin component are shown in Table 16 and FIG. 10.

TABLE 15

| | | | Time (min) | | | | | | |
|---|---|---|---|---|---|---|---|---|---|
| Polmacoxib | | | 0 | 5 | 10 | 15 | 30 | 45 | 60 |
| Example 6 | Water | Average | 0 | 92.6 | 94.0 | 93.9 | 93.8 | 94.7 | 95.2 |
| Control (Acelex tab) | | Average | 0 | 49.0 | 65.9 | 73.9 | 86.1 | 90.3 | 97.0 |

TABLE 16

| Pregabalin | | | Time (min) | | | | | | |
|---|---|---|---|---|---|---|---|---|---|
| | | | 0 | 5 | 10 | 15 | 30 | 45 | 60 |
| Example 6 | pH 1.2 | Average | 0 | 97.8 | 98.3 | 98.7 | 99.7 | 99.3 | 100.4 |
| Control (Lyrica cap) | | Average | 0 | 78.4 | 94.0 | 98.8 | 99.6 | 99.4 | 98.8 |

Example 7

A double-layered composite tablet containing a pregabalin layer exhibiting sustained release and a polmacoxib-pregabalin layer exhibiting immediate release was prepared. In the upper layer which is the immediate release layer, the amount of the main component polmacoxib and the ½ amount of pregabalin were added to exhibit immediate release, and in the lower layer which is the sustained-release layer, the ½ amount of pregabalin and sustained-release agents were added. As the sustained-release agent, hydroxyl propyl methyl cellulose, carbomer and PEO were used.

TABLE 17

| Polmacoxib-pregabalin complex (Example 7) | | | | |
|---|---|---|---|---|
| Upper layer | Manufacturing process | Purpose | Material | per tablet (mg) |
| 1 | Granulation | Main ingredient | Polmacoxib | 2 |
| 2 | | Main ingredient | Pregabalin | 75 |
| 3 | | Excipient | D-mannitol | 113 |
| 4 | | Binder | Hydroxypropyl cellulose | 6 |
| 5 | | Solvent | Ethanol | 60 |
| 6 | Post-mixing | Disintegrant | Sodium croscarmellose | 20 |
| 7 | | Lubricant | Magnesium stearate | 4 |
| | Total weight of immediate release layer | | | 220 |
| Lower layer | Manufacturing process | Purpose | Material | per tablet (mg) |
| 8 | Granulation | Main ingredient | Pregabalin | 75 |
| 9 | | Excipient | Microcrystalline cellulose102 | 60 |
| 10 | | Sustained-release agent | Hydroxy propyl methyl cellulose 2208 | 300 |
| 11 | | Binder | Hydroxypropyl cellulose | 30 |
| 12 | | Solvent | Ethanol | 60 |
| 13 | Post-mixing | Sustained-release agent | Carbomer | 15 |
| 14 | | Sustained-release agent | PEO | 100 |
| 15 | | Excipient | Sodium hydrogen carbonate | 80 |
| 16 | | Lubricant | Magnesium stearate | 5 |
| | Total weight of sustained release layer | | | 665 |
| | Total weight of tablet | | | 885 |

Example 8

Composite tablets were prepared in the same manner as in Example 7, except that the composition of Table 18 was used. As a sustained release agent, hydroxy propyl methyl cellulose, sodium alginate and sodium carboxy methyl cellulose were used.

TABLE 18

| Polmacoxib-pregabalin complex (Example 8) | | | | |
|---|---|---|---|---|
| Upper layer | Manufacturing process | Purpose | Material | per tablet (mg) |
| 1 | Granulation | Main ingredient | Polmacoxib | 2 |
| 2 | | Main ingredient | Pregabalin | 75 |
| 3 | | Excipient | D-mannitol | 113 |

TABLE 18-continued

| | | Polmacoxib-pregabalin complex (Example 8) | | |
|---|---|---|---|---|
| 4 | | Binder | Hydroxypropyl cellulose | 6 |
| 5 | | Solvent | Ethanol | 60 |
| 6 | Post-mixing | Disintegrant | Sodium croscarmellose | 20 |
| 7 | | Lubricant | Magnesium stearate | 4 |
| | Total weight of immediate release layer | | | 220 |

| Lower layer | Manufacturing process | Purpose | Material | per tablet (mg) |
|---|---|---|---|---|
| 8 | Granulation | Main ingredient | Pregabalin | 75 |
| 9 | | Sustained-release agent | Sodium alginate | 150 |
| 10 | | Sustained-release agent | Hydroxy propyl methyl cellulose 2208 | 270 |
| 11 | | Sustained-release agent | Sodium carboxy methyl cellulose | 70 |
| 12 | | Binder | Hydroxypropyl cellulose | 30 |
| 13 | | Solvent | Ethanol | 60 |
| 14 | Post-mixing | Excipient | Sodium hydrogen carbonate | 80 |
| 15 | | Lubricant | Magnesium stearate | 10 |
| | Total weight of sustained release layer | | | 685 |
| | Total weight of tablet | | | 905 |

Experimental Example 7

Figure 11:
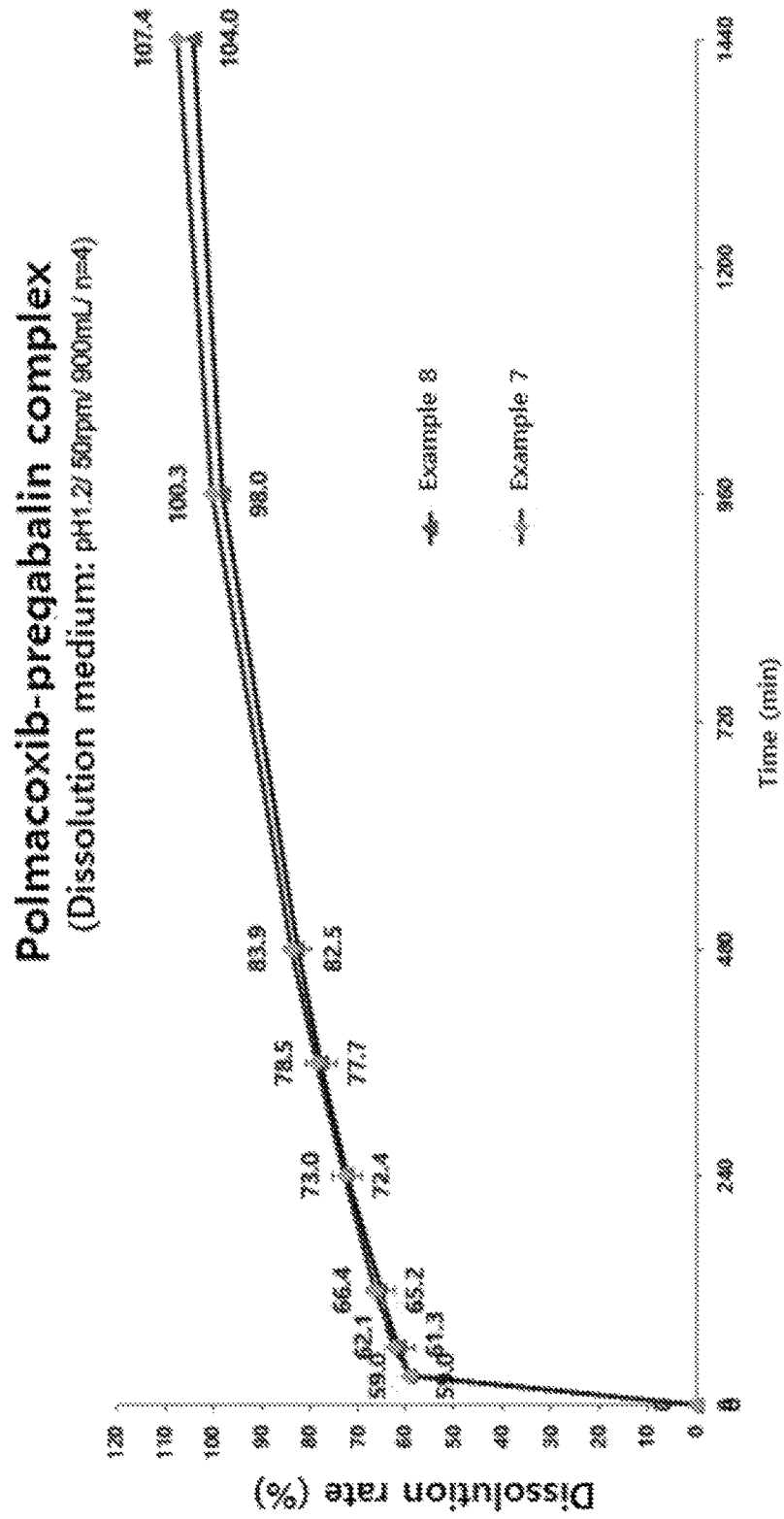
FIG. 11 is a graph showing the comparative dissolution pattern of Experimental Example 7.

Comparative dissolution test was conducted on the formulations of Examples 7 and 8 in the same manner as in Experimental Example 1 and the results are shown in Table 19 and FIG. 11.

TABLE 19

| | | | Time (min) | | | | | | | |
|---|---|---|---|---|---|---|---|---|---|---|
| | | | 0 | 30 | 60 | 120 | 240 | 360 | 480 | 960 | 1440 |
| Example 7 | pH 1.2 | Avg. | 0 | 59.0 | 62.1 | 66.4 | 73.0 | 78.5 | 83.9 | 100.3 | 107.4 |
| Example 8 | | Avg. | 0 | 59.0 | 61.3 | 65.2 | 72.4 | 77.7 | 82.5 | 98.0 | 104.0 |

Experimental Example 8

Figure 12:
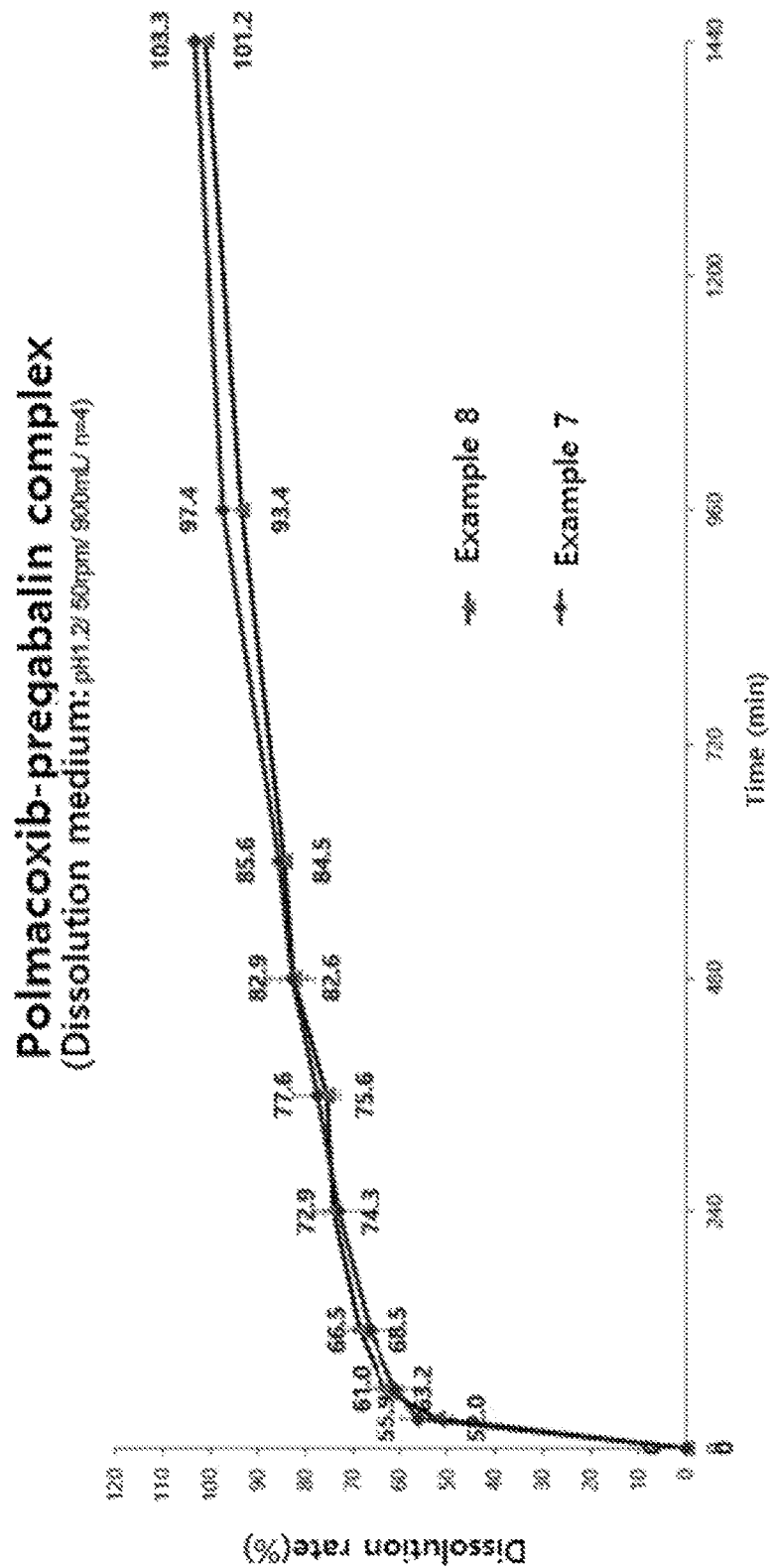
FIG. 12 is a graph showing the comparative dissolution pattern of Experimental Example 8.

Comparative dissolution test was conducted on the formulations of Examples 7 and 8 in the same manner as in Experimental Example 1 by increasing the speed of dissolution paddle from 50 rpm to 100 rpm in order to measure gastrointestinal motility resistance. The results are shown in Table 20 and FIG. 12.

TABLE 20

| | | | Time (min) | | | | | | | |
|---|---|---|---|---|---|---|---|---|---|---|
| rpm 100 | | | 0 | 30 | 60 | 120 | 240 | 360 | 480 | 960 | 1440 |
| Example 7 | pH 1.2 | Average | 0 | 55.9 | 61.0 | 66.5 | 72.9 | 77.6 | 82.9 | 97.4 | 103.3 |
| Example 8 | | Average | 0 | 52.0 | 63.2 | 68.5 | 74.3 | 75.6 | 82.6 | 93.4 | 101.2 |

As shown in the table, the change in the dissolution rate according to the change in the rotational speed is within a range of from 4 to 8%, so it is considered that the possibility of rapid drug release due to the movement of the gastrointestinal tract is low.

Experimental Example 9

Figure 13:
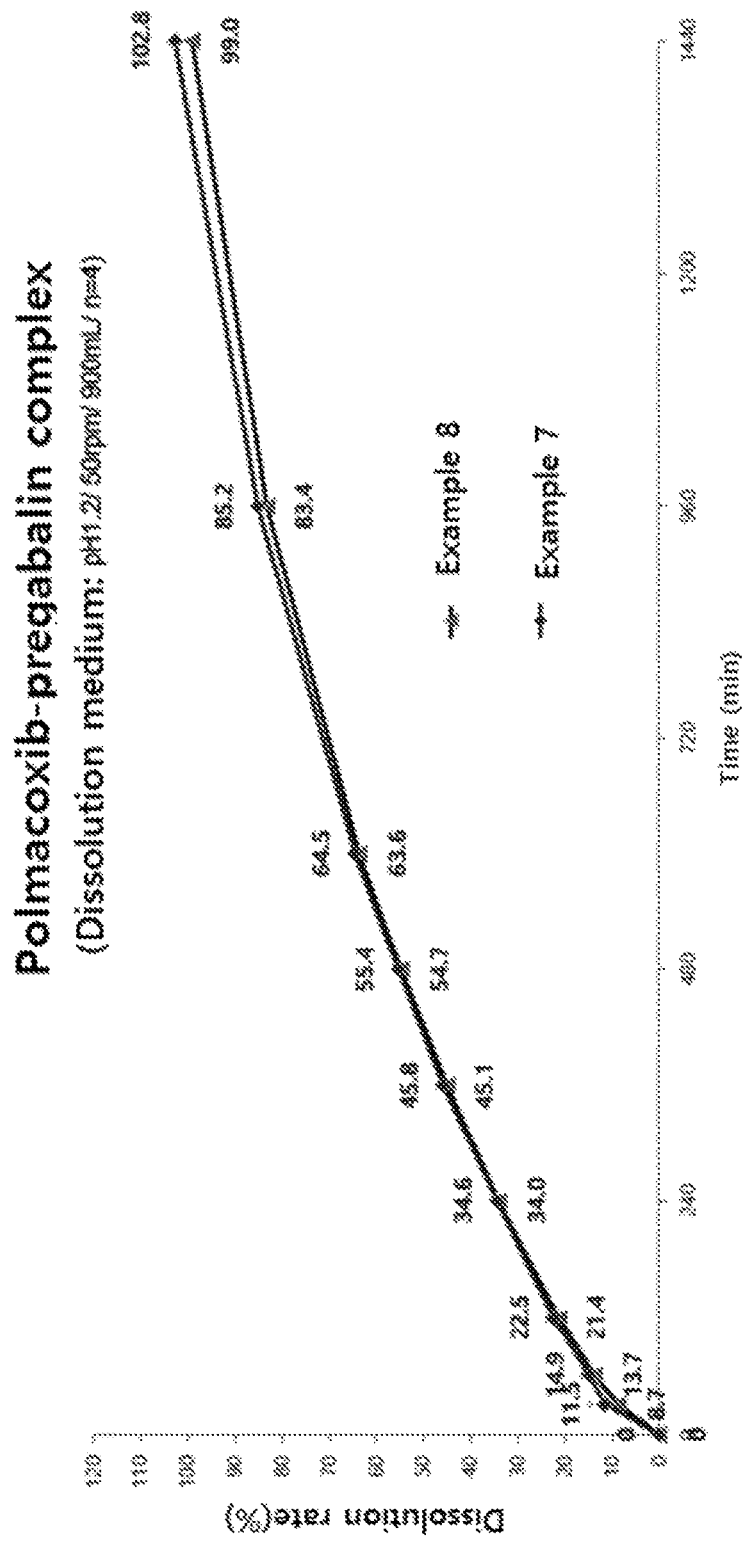
FIG. 13 is a graph showing the comparative dissolution pattern of Experimental Example 9.

Tablets were prepared with only the composition of the sustained-release layer of the compositions of Examples 7 and 8, and the dissolution test was conducted in the same manner as in Experimental Example 1. The overall dissolution result of pregabalin of the bilayer tablet showed the release form of controlled-release (CR) rather than the sustain-release (SR), and a dissolution test was conducted to confirm the dissolution pattern of the lower layer that is the sustained-release part. The results are shown in Table 21 and FIG. 13.

TABLE 21

| Lower layer | | | Time (min) | | | | | | | | |
|---|---|---|---|---|---|---|---|---|---|---|---|
| | | 0 | 30 | 60 | 120 | 240 | 360 | 480 | 600 | 960 | 1440 |
| Example 7 pH 1.2 | Average | 0 | 11.5 | 14.9 | 22.5 | 34.6 | 45.8 | 55.4 | 64.5 | 85.2 | 102.8 |
| Example 8 | Average | 0 | 8.7 | 13.7 | 21.4 | 34.0 | 45.1 | 54.7 | 63.6 | 83.4 | 99.0 |

Examples 9 and 10

Pregabalin in the bilayer composite composition was added to the sustained release layer without distributing into upper and lower layers of immediate release layer and sustained release layer to prepare tablets with the composition shown in Table 22. Since sodium alginate, a sustained-release agent, can change properties of the composition by moisture absorption during the stability test, hydroxyl propyl methyl cellulose, carbomer and PEO were used as a sustained-release agent.

TABLE 22

| | | Polmacoxib-pregabalin complex | | Example 9 | Example 10 |
|---|---|---|---|---|---|
| Upper layer | Manufacturing process | Purpose | Material | per tablet (mg) | |
| 1 | Granulation | Main ingredient | Polmacoxib | 2 | 2 |
| 2 | | Excipient | D-mannitol | 188 | 188 |
| 3 | | Binder | Hydroxypropyl cellulose | 6 | 6 |
| 4 | | Solvent | Ethanol | 60 | 60 |
| 5 | Post-mixing | Disintegrant | Sodium croscarmellose | — | — |
| 6 | | Lubricant | Magnesium stearate | 4 | 4 |
| | | Total weight of immediate release layer | | 200 | 200 |
| Lower layer | Manufacturing process | Purpose | Material | per tablet (mg) | |
| 7 | Granulation | Main ingredient | Pregabalin | 150 | 150 |
| 8 | | Sustained-release agent | Hydroxy propyl methyl cellulose 2208 | 300 | 300 |
| 9 | | Binder | Hydroxypropyl cellulose | 20 | 20 |
| 10 | | Solvent | Ethanol | 300 | 300 |
| 11 | Post-mixing | Excipient | Sodium hydrogen carbonate | 50 | 50 |
| 12 | | Sustained-release agent | PEO | 30 | — |
| 13 | | Sustained-release agent | Carbomer | — | 30 |
| 14 | | Lubricant | Magnesium stearate | 5 | 5 |
| | | Total weight of sustained release layer | | 555 | 555 |
| | | Total weight of tablet | | 755 | 755 |

Experimental Example 10

Figure 14:
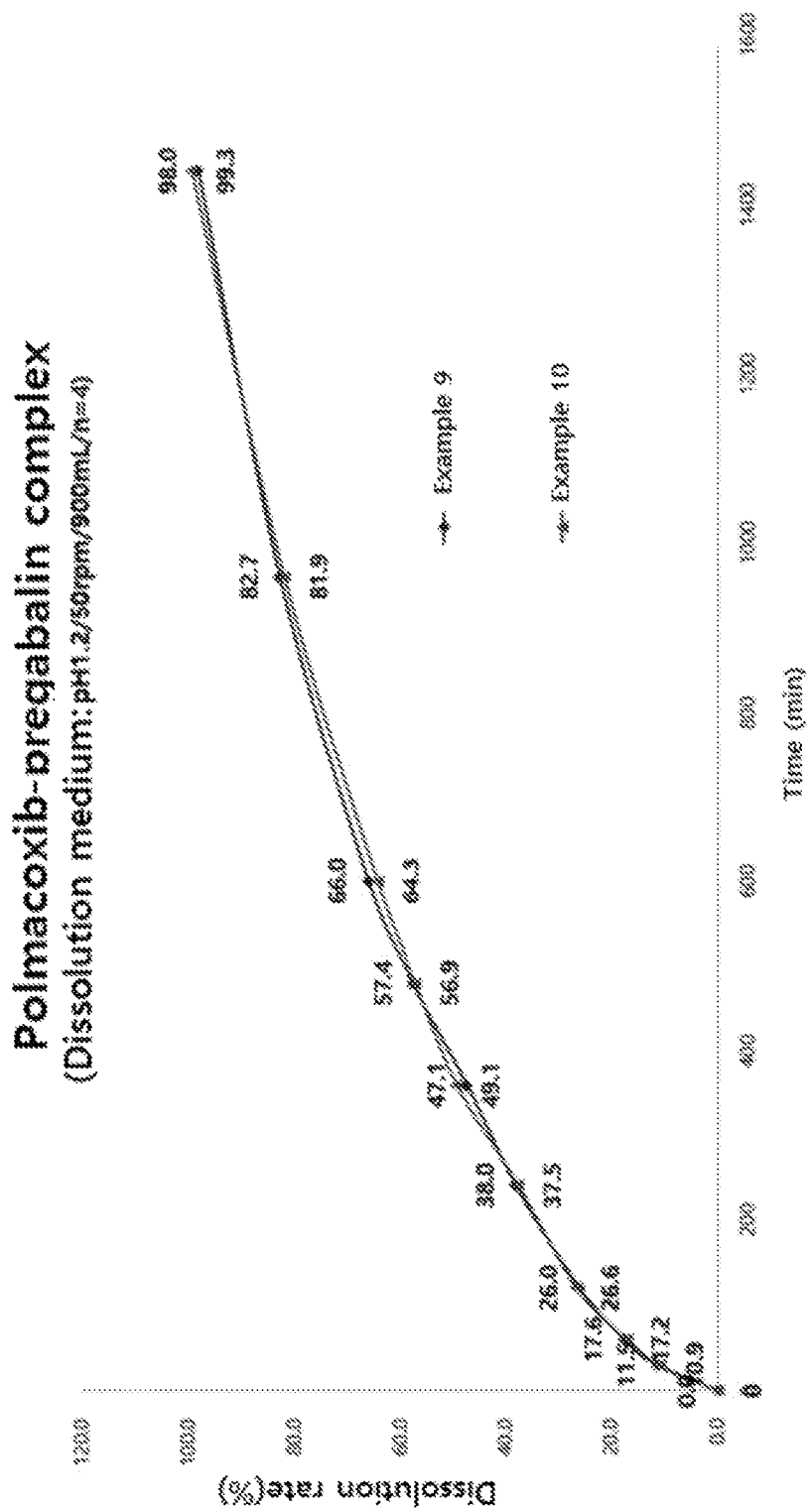
FIG. 14 is a graph showing the comparative dissolution pattern of Experimental Example 10.

A dissolution test was conducted on the tablets according to Examples 9 and 10 in the same manner as in Experimental Example 1. The results are shown in Table 23 and FIG. 14.

TABLE 23

| | | Time (min) | | | | | | | | | | |
|---|---|---|---|---|---|---|---|---|---|---|---|---|
| pH 1.2 | | 0 | 30 | 60 | 120 | 240 | 360 | 480 | 540 | 600 | 720 | 960 | 1440 |
| Example 9 | Avg | 0 | 11.5 | 17.6 | 26.0 | 38.0 | 47.1 | 57.4 | — | 66.0 | — | 82.7 | 98.0 |
| Example 10 | Avg | 0 | 10.9 | 17.2 | 26.6 | 37.5 | 49.1 | 56.9 | — | 64.3 | — | 81.9 | 99.3 |

Example 11

The optimal composition was selected based on the results of Experimental Example 10. Tablets were prepared according to the composition in Table 24 in order to prepare a composition for reducing the size of the tablet without affecting the dissolution rate. As shown in the table, the weight of the final tablet was reduced by reducing the content of excipients contained in the sustained release layer while simultaneously reducing the amount of the immediate release layer. In addition, in order to improve instability due to tableting pressure of the pregabalin main component, formulations were prepared with different tablet hardness. Specifically, tablets having hardness of 5 kp and 9 kp were prepared, respectively.

TABLE 24

| | | Polmacoxib-pregabalin complex | | Example 11 |
|---|---|---|---|---|
| Upper layer | Manufacturing process | Purpose | Material | per tablet (mg) |
| 1 | Granulation | Main ingredient | Polmacoxib | 2 |
| 2 | | Excipient | D-mannitol | 100 |
| 3 | | Binder | Hydroxypropyl cellulose | 5 |
| 4 | | Solvent | Ethanol | 50 |
| 5 | Post-mixing | Lubricant | Magnesium stearate | 3 |
| | | Total weight of immediate release layer | | 110 |
| Lower layer | Manufacturing process | Purpose | Material | per tablet (mg) |
| 6 | Granulation | Main ingredient | Pregabalin | 150 |
| 7 | | Sustained-release agent | Hydroxy propyl methyl cellulose 2208 | 230 |
| 8 | | Binder | Hydroxypropyl cellulose | 20 |
| 9 | | Solvent | Ethanol | 200 |
| 10 | Post-mixing | Excipient | Sodium hydrogen carbonate | 35 |
| 11 | | Sustained-release agent | PEO | 25 |
| 12 | | Lubricant | Magnesium stearate | 5 |
| | | Total weight of sustained release layer | | 465 |
| | | Total weight of tablet | | 575 |

Experimental Example 11

Figure 15:
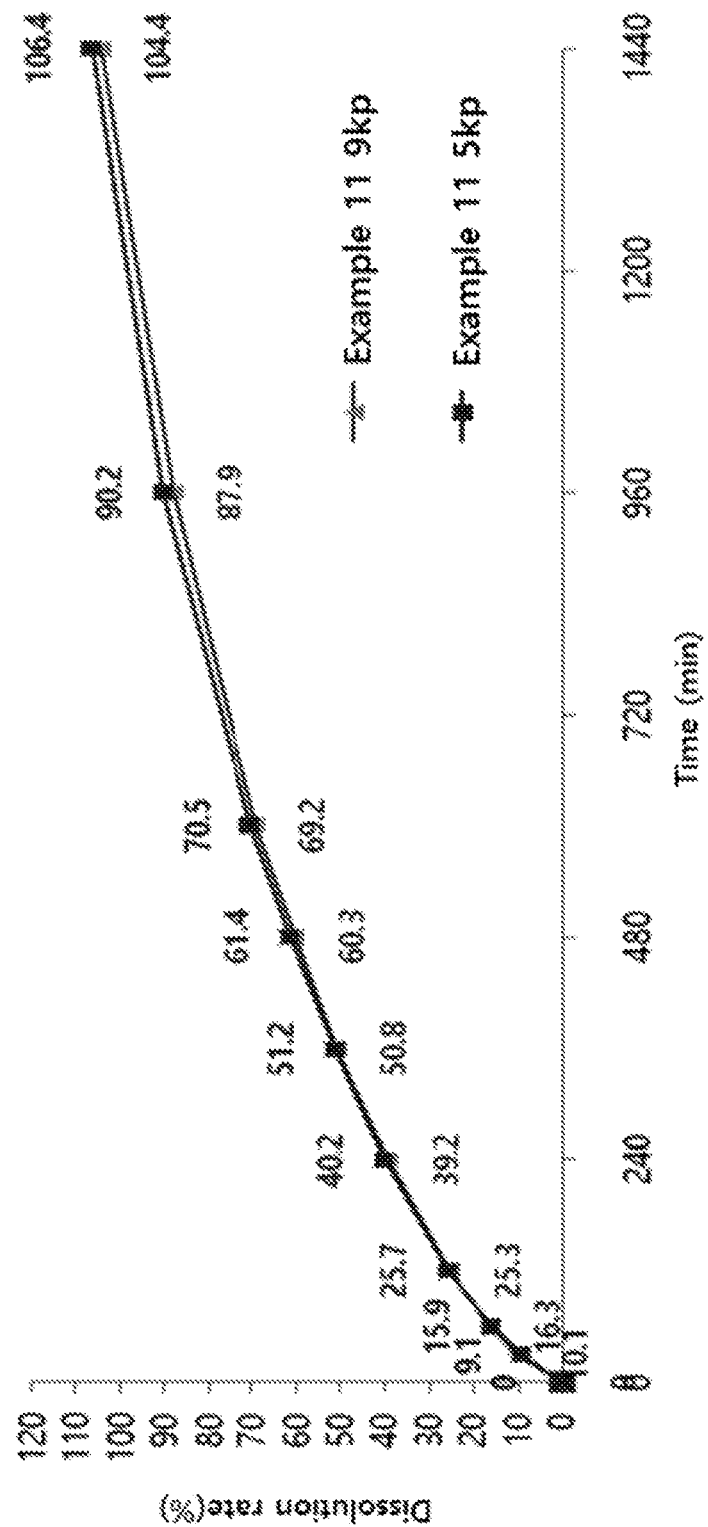
FIG. 15 is a graph showing the comparative dissolution pattern of Experimental Example 11.

Since pregabalin main component has instability due to tableting pressure, a dissolution test was conducted on the formulation of Example 11 with different hardness. The results are shown in Table 25 and FIG. 15.

TABLE 25

| | | Time (min) | | | | | | | | | | | |
|---|---|---|---|---|---|---|---|---|---|---|---|---|---|
| pH 1.2 | | 0 | 30 | 60 | 120 | 240 | 360 | 480 | 540 | 600 | 720 | 960 | 1440 |
| Example 11 (5 kp) | Avg. | 0 | 9.1 | 15.9 | 25.7 | 40.2 | 51.2 | 61.4 | — | 70.5 | — | 90.2 | 106.4 |
| Example 11 (9 kp) | Avg. | 0 | 10.0 | 16.3 | 25.3 | 39.2 | 50.8 | 60.3 | — | 69.2 | — | 87.9 | 104.4 |

As shown in the table, as a result of dissolution test of tablets with different hardness, it can be confirmed that the dissolution rate according to tableting pressure is not significantly different. In addition, with the results of Experimental Examples 10 and 11, it can be confirmed that reducing the content of excipients in order to reduce the size of the tablet does not result in significant difference in the dissolution rate.

Example 12

Tablets were prepared with the composition shown in Table 26 by appropriately increasing the mass of the upper layer in order to improve the problem of mass deviation and non-uniform content of tablets after production due to the low content of the upper layer composition containing polmacoxib when manufacturing tablets in a scale up production facility.

TABLE 26

| Polmacoxib-pregabalin complex | | | | Example 12 |
|---|---|---|---|---|
| Upper layer | Manufacturing process | Purpose | Material | per tablet (mg) |
| 1 | Granulation | Main ingredient | Polmacoxib | 2 |
| 2 | | Excipient | D-mannitol | 130 |
| 3 | | Disintegrant | Sodium croscarmellose | 10 |
| 4 | | Binder | Hydroxypropyl cellulose | 5 |
| 5 | | Solvent | Ethanol | 30 |
| 6 | Post-mixing | Lubricant | Magnesium stearate | 3 |
| | Total weight of immediate release layer | | | 150 |
| Lower layer | Manufacturing process | Purpose | Material | per tablet (mg) |
| 6 | Granulation | Main ingredient | Pregabalin | 150 |
| 7 | | Sustained-release agent | Hydroxy propyl methyl cellulose 2208 | 200 |
| 8 | | Binder | Hydroxypropyl cellulose | 20 |
| 9 | | Solvent | Ethanol | 140 |
| 10 | Post-mixing | Excipient | Sodium hydrogen carbonate | 50 |
| 11 | | Sustained-release agent | PEO | 50 |
| 12 | | Lubricant | Magnesium stearate | 5 |
| | Total weight of sustained release layer | | | 475 |
| | Total weight of tablet | | | 625 |

Experimental Example 12

Figure 16:
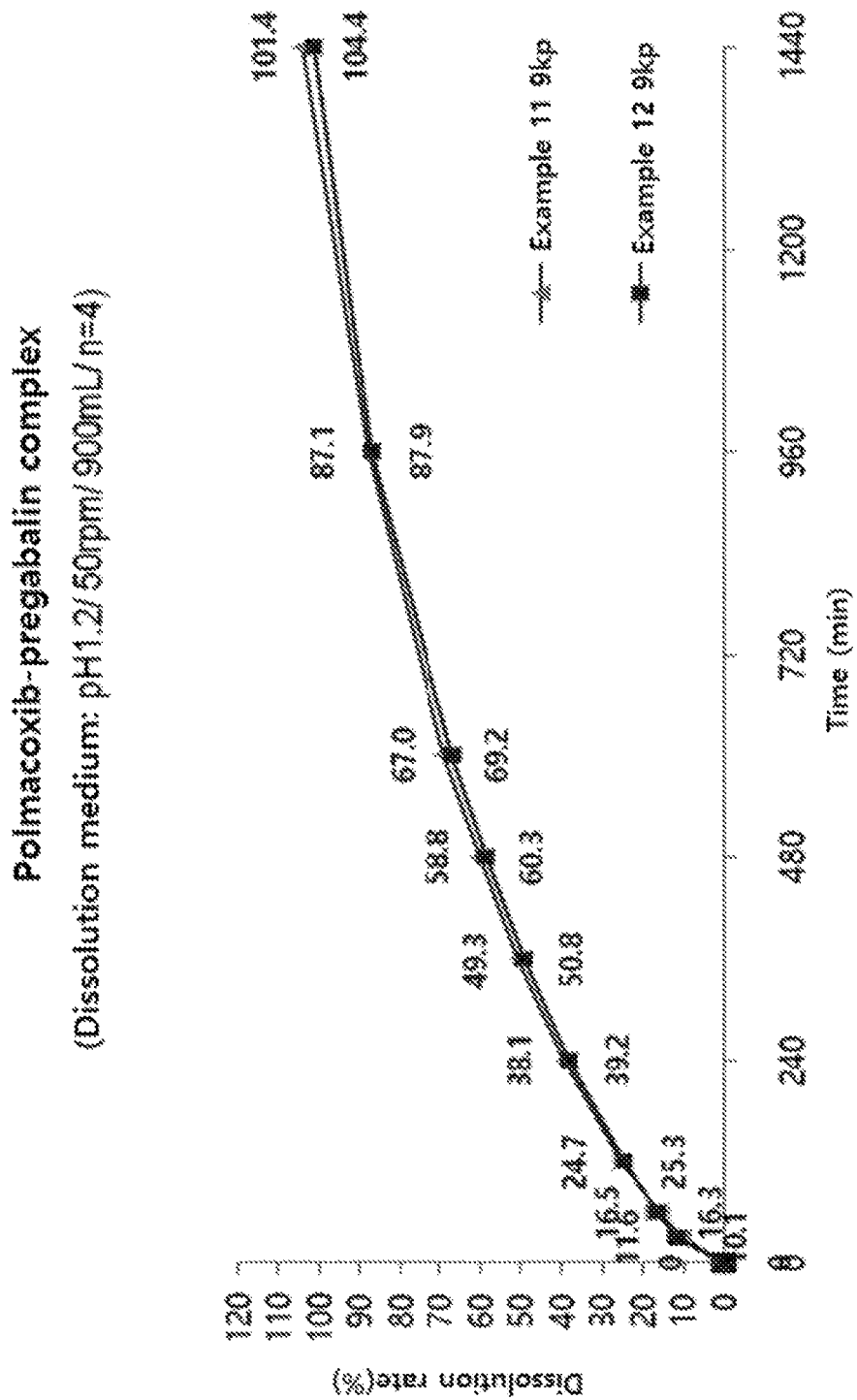
FIG. 16 is a graph showing the comparative dissolution pattern of pregabalin of Experimental Examples 11 and 12.
Figure 17:
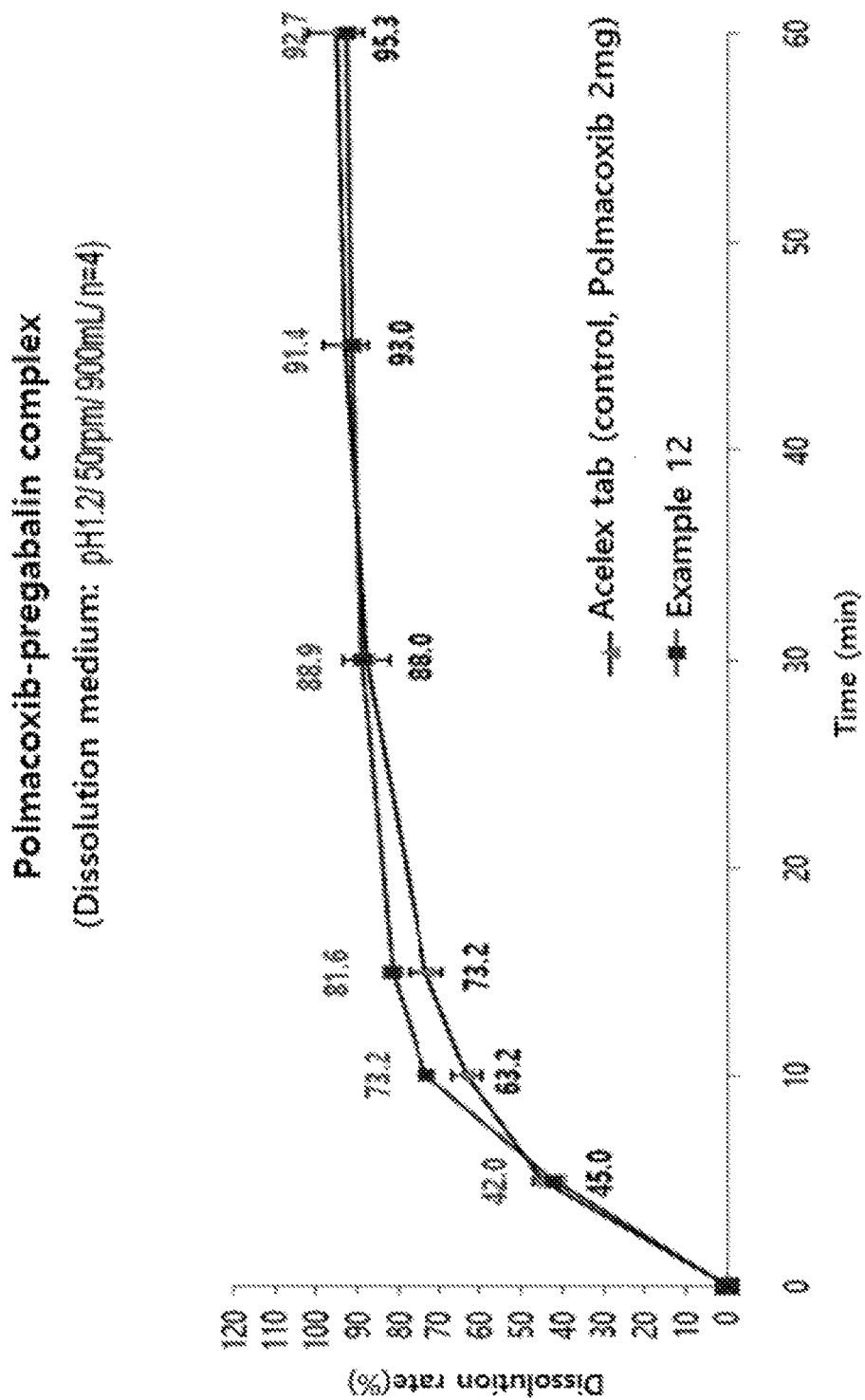
FIG. 17 is a graph showing the comparative dissolution pattern of polmacoxib of Experimental Example 12.

A dissolution test was conducted on the tablets of Example 11 and Example 12 in the same manner as in Experimental Example 11. The results of the comparative dissolution test for the pregabalin component are shown in Table 27 and FIG. 16 and the results of the comparative dissolution test for the polmacoxib component are shown in Table 28 and FIG. 17.

TABLE 27

| | | Time (min) | | | | | | | | | | | |
|---|---|---|---|---|---|---|---|---|---|---|---|---|---|
| pH 1.2 | | 0 | 30 | 60 | 120 | 240 | 360 | 480 | 540 | 600 | 720 | 960 | 1440 |
| Example 12 (9 kp) | Avg. | 0 | 11.6 | 16.5 | 24.7 | 38.1 | 49.3 | 58.8 | — | 67.0 | — | 87.1 | 101.4 |
| Example 11 (9 kp) | Avg. | 0 | 10.1 | 16.3 | 25.3 | 39.2 | 50.8 | 60.3 | — | 69.2 | — | 87.9 | 104.4 |

TABLE 28

| | | Time (min) | | | | | | |
|---|---|---|---|---|---|---|---|---|
| pH 1.2 | | 0 | 5 | 10 | 15 | 30 | 45 | 60 |
| Example 12 | Average | 0 | 45.0 | 63.2 | 73.2 | 88.0 | 93.0 | 95.3 |
| Control Acelex tablet | Average | 0 | 42.0 | 73.2 | 81.6 | 88.9 | 91.4 | 92.7 |

As described above, it can be seen that the composition according to the present invention has a similar drug release pattern to a commercially available oral formulation containing pregabalin, Lyrica capsule, and Acelex tablet. It was found that in formulating polmacoxib and pregabalin into one single dosage form, there is no interaction between the two drugs in a single dosage form and it can be designed to exert the effect of each drug mutually complementary and sustainably by taking once or twice a day. In addition, since pregabalin may cause stability problems due to the increased related substances by external physical factors such as tableting pressure, an appropriate tableting pressure was applied in order to compensate for this. It was confirmed that the tablet dosage form may be superior to the capsule dosage form in terms of stability in the production of the formulation. In addition, in the case of the capsule dosage form, it was confirmed that the uniformity was relatively excellent without any variation in mass when filling as flowability of particles was excellent. In addition, it confirmed the possibility of a composite having a double-layered formulation of a pregabalin sustained-release layer and a polmacoxib immediate-release layer that can reduce the number of doses, in addition to a single complex immediate release tablet.

The above description is merely illustrative of the technical idea of the present invention, and various modifications and variations can be made by those skilled in the art without departing from the essential characteristics of the present invention. In addition, the embodiments disclosed in the present invention are not intended to limit the technical idea of the present invention but to describe the present invention, and the scope of the technical idea of the present invention is not limited by these embodiments. The protection scope of the present invention should be interpreted by the following claims, and all technical ideas within the scope equivalent thereto should be construed as being included in the scope of the present invention.

What is claimed is:

1. A pharmaceutical composition comprising polmacoxib and pregabalin for the treatment of pain,
    wherein the weight ratio of polmacoxib to pregabalin is from 1:1 to 1:300,
    wherein the pharmaceutical composition comprises 0.1% to 10% by weight of polmacoxib and 10% to 50% by weight of pregabalin based on the total weight of the pharmaceutical composition, and
    wherein the composition comprises 1 mg to 5 mg polmacoxib.

2. The pharmaceutical composition according to claim 1, wherein the pain comprises acute or chronic pain caused by inflammation or neuropathy.

3. The pharmaceutical composition according to claim 1, wherein the pain comprises neurogenic pain, diabetic neuropathy, pain caused by generalized anxiety disorder, fibromyalgia, hyperalgesia, allodynia, cancer pain, osteoarthritis, rheumatoid arthritis, spondylitis, frozen shoulder, lumbodynia, or sciatica.

4. The pharmaceutical composition according to claim 1, wherein the pharmaceutical composition comprises 0.3% to 1% by weight of polmacoxib based on the total weight of the pharmaceutical composition.

5. The pharmaceutical composition according to claim 1, wherein the composition further comprises a pharmaceutically acceptable excipient.

6. The pharmaceutical composition according to claim 5, wherein the excipient comprises one or more compounds selected from the group consisting of ethyl cellulose, hydroxy propyl cellulose, hydroxy propyl methyl cellulose, sodium carboxy methyl cellulose, polyethylene oxide, carbomer, sodium alginate, mannitol, sodium croscarmellose, sodium hydrogen carbonate and magnesium stearate.

7. The pharmaceutical composition according to claim 1, wherein the composition is in the form of a tablet, a capsule or a suspension.

8. The pharmaceutical composition according to claim 7, wherein the tablet, the capsule, or the suspension comprises a mixture of polmacoxib and pregabalin.

9. The pharmaceutical composition according to claim 1, wherein the composition is in the form of a double-layered tablet having a bi-layered structure or a multi-layered tablet having a multi-layered structure in which polmacoxib, pregabalin or a mixture thereof is separated into each individual layer.

10. The pharmaceutical composition according to claim 1, wherein the composition is in the form of a double-layered tablet comprising a sustained release layer and an immediate release layer.

11. The pharmaceutical composition according to claim 10, wherein the sustained release layer comprises pregabalin and the immediate release layer comprises polmacoxib.

12. The pharmaceutical composition according to claim 1, wherein the composition further comprises a pharmaceutically acceptable coating base or a pharmaceutically acceptable carrier.

13. The pharmaceutical composition of claim 1, wherein the composition comprises 75 mg to 300 mg pregabalin.

14. The pharmaceutical composition according to claim 1, wherein the composition comprises 1 mg to 2 mg polmacoxib.

15. The pharmaceutical composition according to claim 14, wherein the composition comprises 75 mg to 150 mg pregabalin.

16. The pharmaceutical composition according to claim 1, wherein polmacoxib is in an immediate release layer.

17. The pharmaceutical composition according to claim 13, wherein pregabalin is in a sustained release layer, or pregabalin is in both an immediate release layer and a sustained release layer.

18. The pharmaceutical composition according to claim 14, wherein polmacoxib is in an immediate release layer.

19. The pharmaceutical composition according to claim 15, wherein pregabalin is in a sustained release layer, or pregabalin is in both an immediate release layer and a sustained release layer.

* * * * *